US 8,800,970 B2

(12) United States Patent
Heine et al.

(10) Patent No.: US 8,800,970 B2
(45) Date of Patent: Aug. 12, 2014

(54) METHODS AND DEVICES IN THE FIELD OF TREATMENT WITH MEDICAL GASES

(75) Inventors: Daniel Heine, Pfalzgrafenweiler (DE); Markus Gruendler, Freudenstadt (DE); Christoph Gruendler, Freudenstadt (DE); Philipp Hiereth, Baden-Baden (DE); Martin Busch, Horb a. N. (DE)

(73) Assignee: Gründler GmbH, Freudenstadt (DE)

( * ) Notice: Subject to any disclaimer, the term of this patent is extended or adjusted under 35 U.S.C. 154(b) by 330 days.

(21) Appl. No.: 13/296,518

(22) Filed: Nov. 15, 2011

(65) Prior Publication Data

US 2012/0146251 A1   Jun. 14, 2012

(30) Foreign Application Priority Data

Nov. 15, 2010   (DE) .......................... 10 2010 051 183
Nov. 15, 2010   (DE) .......................... 10 2010 051 187
Nov. 15, 2010   (DE) .......................... 10 2010 051 188
Nov. 15, 2010   (DE) .......................... 10 2010 051 189
Nov. 15, 2010   (DE) .......................... 10 2010 051 191

(51) Int. Cl.
*B01F 3/04*   (2006.01)

(52) U.S. Cl.
USPC ...................... 261/26; 261/119.1; 128/204.17

(58) Field of Classification Search
CPC .......... B01F 3/04; A61M 16/16; A61M 16/14
USPC .............................. 261/26, 119.1; 128/204.17
See application file for complete search history.

(56) References Cited

U.S. PATENT DOCUMENTS 8,240,306 B2 *   8/2012   Cortez et al. ............. 128/203.27
2006/0151624 A1   7/2006   Grundler et al.
2008/0105257 A1   5/2008   Klasek et al.

FOREIGN PATENT DOCUMENTS

EP   1 901 011   3/2008
GB   2 002 238   2/1979
WO   2008/055307   5/2008

OTHER PUBLICATIONS

International Search Report and Written Opinion issued in corresponding PCT Application No. PCT/EP2011/070163, mailed Aug. 24, 2012, 12 pages.

* cited by examiner

*Primary Examiner* — Robert A Hopkins
(74) *Attorney, Agent, or Firm* — Nixon & Vanderhye, P.C.

(57) ABSTRACT

The present invention relates to a humidifier for humidifying medical gases, comprising a humidification module including a control unit, wherein the humidification module is adapted for receiving a humidification chamber. Furthermore, the humidification module is further adapted to sense and/or receive information upon connection of the humidification chamber and/or additional equipment such as hoses, power supply pack.

39 Claims, 11 Drawing Sheets

METHODS AND DEVICES IN THE FIELD OF TREATMENT WITH MEDICAL GASES

This application claims priority to DE Application No. 10 2010 051 187.0, filed Nov. 15, 2010; DE Application No. 10 2010 051 188.9, filed Nov. 15, 2010; DE Application No. 10 2010 051 189.7, filed Nov. 15, 2010; DE Application No. 10 2010 051 183.8, filed Nov. 15, 2010; and DE Application No. 10 2010 051 191.9, filed Nov. 15, 2010, the entire contents of each of which are hereby incorporated by reference.

The present invention relates to different preferred technologies such as methods and devices in the field of treatment of patients by medical gases and humidifying medical gases, such as in the fields of treating various respiratory disorders, providing artificial ventilation, or treating sleep disordered breathing (SDB), e.g. by means of therapies such as Continuous Positive Airway Pressure (CPAP). The invention e.g. includes a humidifier, a method for operation of such humidifier, particularly a method for, preferably automatic, adaptation of a humidifier's operation, a humidification chamber and a method for manufacturing such chamber as well as a method and device for the temperature-controlled electrical heating of tube assemblies for medical gases.

In the following preferred technologies of the present invention will be discussed, such as technologies related to a universal humidifier, an illuminated humidifier chamber, a temperature-controlled electrical heating of tube assemblies for medical gases, particularly of respiration tubes, a heating and/or control device for respiration tubes, and/or an improved sealing of the bottom and/or lid of humidifier chambers. It will be readily apparent, that different aspects of the individual technologies discussed herein may well be combined to achieve preferred solutions.

Various technical solutions are available for heating and humidifying medical gases, in particular for artificial respiration and respiration therapy as well as for the continuous or intermittent insufflation into the airways or into body cavities or organs, each of said solutions being optimized for specific applications.

The heating and humidification of medical gases, in particular for artificial respiration and respiration therapy as well as the continuous or intermittent insufflation in the airways or in body cavities or organs has, for several years, in many fields been an accepted necessity for minimizing side effects caused by dehydration and cooling down.

A plurality of so-called respiration therapy devices such as CPAP and bi-level systems are common on the market for the therapy of sleep-related respiratory disorders, wherein the delimitation from so-called respiration devices becomes more and more indistinct. It is also known that patient comfort and the success of the therapy can be improved by humidifying the supplied respiratory gases. For this reason, a large number of humidifiers exist which can be coupled with the above-mentioned respiration therapy devices. It is known that the effectiveness of the humidification can be increased considerably by heating the water.

Commonly active respiratory gas humidifiers which consist at least of an electro-medical control, regulation and operating unit (in the following referred to as humidifier), a humidifier chamber (optionally also in the form of a humidifier cylinder or the like) for saturating the gas with water vapor and at least one typically heated respiration tube are used.

For heating and humidifying medical gases, in particular for artificial respiration and respiration therapy, essentially, i.a., the following solutions are known and established:

1. passover humidification (e.g. by Fisher & Paykel), optionally combined with wick evaporator and/or bubble part
2. counter-flow humidification (Grundler HumiCare)
3. fluid contact by means of membranes (e.g. Dräger Aquamod)
4. flash evaporator (e.g. Pari Omni Hydrate)
5. bubble humidifier (e.g. Wilamed)

Different kinds of humidification or humidification concepts are discussed in EP 1 558 877 A1 the content of which is incorporated herein by reference.

As stated above, in any of the mentioned embodiments, devices for humidifying respiratory gases consist of or comprise a central unit with control and operating unit, a humidifier chamber as well as optionally further auxiliary equipment such as heated tubes etc.

Currently, if a user selects a specific product, he/she is also bound to a specific humidification technology, which restricts the respective flexibility of use, since any one of these technologies has specific advantages and disadvantages as compared to the alternatives (e.g. in teams of trading, handling or function).

Furthermore, the above-mentioned humidifiers are always combined with a power supply unit, which is mostly integrated in the central unit itself. This cost-intensive assembly thus must always be configured so as to suit the electrically most energy-intensive application of the device that is conceivable, which can influence the size and weight in a relevant manner and limit the cost effectiveness if a device is exclusively used in applications which need clearly less energy than the energy that could be provided in view of the dimensioning of the power supply unit.

So far, the above-mentioned solutions can supply at most two external heatable components with energy and control them, so that in some applications further control devices for controlling additional components of the application (e.g. heated filtering collars or heated collars for valves and/or sensors) are necessary.

None of the above-mentioned solutions comprises interfaces which allow a partial or complete (remote) control by connected coupled devices such as monitors or also the remote control of such devices by the humidifier. So far, it is only known to couple the humidifier to respiration devices (e.g. DE 10 2006 045 739 B3) for the purpose of data transmission (such as gas flow rates or the like).

Moreover, the solutions known in the art are of general disadvantage, particularly since they only allow low flexibility of use and thus of therapy.

Humidifiers may include a user interface comprising signal LEDs and acoustic signal generators and/or seven-segment displays or, in modern devices, also a graphic display.

The humidifier chambers are normally disposable or re-usable canisters which are made of a transparent plastic material and in which the water and the gas are in intensive contact. Also in systems with automatic water level regulation, the user must in most cases monitor the correct water level by visual inspection.

Moreover, humidifiers exist in which the water level in the chamber is detected optically or by means of other sensors.

Current signaling alarms and warnings are signaled in different ways via the user interface of the respective device. Depending on the structural design and the environment in which the device is used, it can be difficult to identify the device causing the alarm quickly and clearly. This is applicable at the latest when several equal devices are used in the same room.

In present humidifier chambers, water level may be detected. E.g., a magnet float may be used for detecting a water level that is too high. When the water level is too high, said magnet float triggers a magnet switch located at a respective place in the humidifier chamber, so that an overfilling alarm can be signaled. This solution is technically involved, leads to an increased consumption of resources (for each single humidifier chamber an individual magnet switch is necessary) and causes high unit costs of the humidifier chamber.

Present humidifier chambers use various concepts for limiting the germ contamination. Basic concepts are the limitation of the lifetime of the chamber and/or a prescribed or recommended treatment (in case of re-usable humidifier chambers). These concepts are disadvantageous because, e.g., in view of patients which are given artificial respiration for a long time, the respiration circle must be opened in both concepts for exchanging the humidifier chambers, which is admittedly disadvantageous in terms of hygiene (mainly because of the portal of entry for the germs opened during the exchange).

In present humidifier chambers, the temperature is measured by means of sensors which are placed directly in the medium (gas or fluid) and which are either inserted in a sealing manner in the humidifier chamber or firmly integrated in the humidifier chamber as part thereof. The solution according to which the sensors are inserted is disadvantageous because no consequent single-use concept can be realized and the opening forms a potential port of entry for pathogenic organisms. The solution according to which the sensors are integrated is technically very involved and requires many resources.

Various technical solutions are known for heating and humidifying medical gases, in particular for artificial respiration and respiration therapy and for laparoscopy. In particular in combination with so-called active humidifiers, electrically heated respiration tubes are widespread and well-proven for minimizing the formation of condensate in the tube. These tubes are typically connected by means of an electrical plug-in connection with the humidifier, which then provides the electrical heating power in accordance with the adjustments and monitors the function. There are various kinds of heating tubes, namely tube embodiments in which the heating coils extend in a straight or helical manner in the interior of the tube as well as embodiments in which the tube wall itself is heated. In both cases the heating power of the inspiration tube is controlled on the basis a temperature sensor which is located close to the patient and outside the heating zone and which projects into the lumen of the tube. In very simple embodiments partly also a predetermined heating power is output to the heating conductor in the tube and no temperature control is provided at all. While the heating of the inspiration tube primarily serves for maintaining the suitable temperature/humidity, the heating of expiration tubes primarily serves for avoiding condensate in the expiratory system and, therefore, is less critical in view of a constant temperature at the end of the heating section.

Since the temperature of the heated tubes is controlled by means of sensors at the end of the respective heating section, essentially the temperature of the flowing gas is detected by the sensors. If the gas flow is interrupted for a relatively long time, there is basically the risk that the corresponding tube is overheated or that a heat accumulation occurs therein. This cannot properly be detected by prior art systems with the temperature sensors, particularly those systems not using flow sensors.

In accordance with a commercially available solution to this problem, also a flow sensor is integrated in at least one gas-conducting component, e.g., in the inspiration limb, which sensor detects an interruption of the gas flow elegantly and quickly. In this regard the relatively high costs for such a sensor are problematic, so that the realization as a disposable version is difficult in terms of trading.

Moreover, so far this solution has been realized only for the tube limb extending from the humidifier chamber in the direction of the patient or from the respiration device towards the chamber, but not for the opposite direction (i.e. from the patient to the expiration valve of the respiration device). However, in everyday life there are also situations in which, e.g., by a severe leakage or also by modifications in the respiration setting, the gas flow is (almost) stopped only in the expiration limb while a sufficient gas flow is still flowing through the inspiration limb and/or the humidifier chamber.

In contrast thereto, in practice it unfortunately happens from time to time that when switching on the respiration device or after an interruption of the respiration, the user forgets to also switch on the humidifier so that the humidifier has no electrical function and thus can neither fulfill its task nor output a corresponding alarm because it is switched off.

A higher absolute humidity in the respiratory gas increases the risk that condensate is formed in the respiration tubes and in the patient interface, which can lead to disturbances in the meaning of, e.g., noise generation or incorrect measurements by the therapy device in particular when the temperature of the bedroom is lowered during the night. These deficiencies can be handled by means of thermally insulated and/or heated tubes, as is known, i.a., primarily from the respiration in intensive care units.

Since for these applications most respiration therapy devices and humidifiers do not have an integrated control for heated respiration tubes, in particular no temperature control, there are many patients/users which suffer from the condensate formation when using the devices. Although high-end devices exist which, for this purpose, have an integrated solution with a heated tube, they are often not available to the patient since the doctors prescribe lower-priced standard devices which do not have a tube heating.

A further application in which an undesired formation of condensate can occur during use is the use of heart-lung machines or also of pumpless systems for assisting the lung, in which the blood flows extracorporeally via an exchange membrane, on the opposite side of which a gas flow is passed through. Condensate formation is possible on the gas side, which can lead to a reduction in the exchange surface as well as to an increase in the pressure loss on the gas side. Both problems could also be avoided by using the heated tube according to the technology.

In presently commercially available humidifier chambers it is common practice to connect the housing and the bottom of the chamber with each other by means of sealing elements (e.g. in the form of adhesive or an additional sealing element such as, e.g., an O-ring or specifically shaped elastomeric parts) in order to achieve a pressure- and water-tight connection. This additional sealing element can also be connected firmly to any one of the components (e.g. as two-component injection molded part). In all these construction approaches it is disadvantageous that an additional sealing element is required; hence, an increased amount of resources is required and the complexity is increased so that there is the risk that the robustness is decreased because of failing components. Also, manufacturing expenditure and complexity is increased, going along with an increase in failure and reject rate. In these structures, pressure typically leads to a load on the sealing surface and, if the pressure is applied permanently, there are potentially signs of wear in the meaning of, e.g., leakage, particularly increased leakage. An example for chambers of this kind can be found, e.g., in EP 0 589 429 B1.

The present technology provides an improved humidification chamber and an improved method for manufacturing the same, wherein particularly the disadvantages of the prior art are to be overcome or at least ameliorated.

An embodiment of the present technology describes a universal, modular device which can be configured specifically for the respective particular requirements of individual applications. Also, a corresponding method of adjusting, preferably automatically, to the particular humidification required is described.

A device according to the technology comprises at least one of the following features:

Improvements of humidifiers for medical gases, which either alone or in combination are directed to broadening or improving the field of use, the consumption of resources as well as the functionality.

The present technology provides the option to use or select a humidifier chamber according to various technologies for use in a humidifier unit, as well as to provide further universal external interfaces as well as a connection for an external power supply unit or an external secondary battery, in order to thus provide a much wider coverage of the various required humidification applications.

Thus, a device according to the technology is a universal device for heating and humidifying medical gases (in the following referred to as humidifier), comprising a humidifier unit or humidification module with electric control or a control unit, a humidifier chamber adapted to couple to the control unit, as well as optionally further heated components such as respiration tubes.

An embodiment is characterized in that humidifier chambers according to the passover principle and also various kinds of chambers with active (electromechanically caused) water movement with and without separation of the media by means of a membrane can be used by adjusting the operation and control algorithms to the respective technology used. Different humidification concepts may be used with the present invention, for example:

(1) Pass-Over Humidifiers (e.g. DE 3830314) that use a reservoir filled with heated water. The respiratory gas is conducted along the water's surface thus heating and at the same time humidifying the gas;

(2) Membrane-Type Humidifiers (e.g. DE 4303645) in which gas is directed over the surface of a structured body protruding from the heated fluid. The structured body is sucking from the reservoir the amount of fluid needed, e.g. by capillary forces. Only the amount of fluid to be evaporated is replaced by fresh heated fluid;

(3) Fibre-Type Humidifiers (e.g. DE 19727884) that include a bundle of partially permeable hollow fibers (e.g. from PTFE) and the gas to be heated and humidified is directed through their luminae. The outer surface of the fibers is in contact with the fluid required for humidification;

(4) High-Temperature Humidifiers (e.g. DE 4312793) that evaporate small quantities of fluid at temperatures of about 80° C. to 130° C. that mix with the gas flow, thus providing both the energy to heat the gas and the humidity as required;

(5) Bubble Through Humidifiers (e.g. DE 3730551) in which gas is bubbled through a heated fluid, resulting in heating and humidification of the gas;

(6) Ultrasound-Type Nebulizers (e.g. DE 197 26 110) that use ultrasound to induce fluid vibrations resulting in the generation of tiny droplets which enter the gas flow;

(7) Pressure-Type Nebulizer (e.g. DE 28 34 622) that nebulize a fluid resulting in the formation of tiny droplets, not molecular fluid;

(8) Heat and Moisture Exchangers ("HME" e.g. DE 94 17 169), Filter Pads, etc. ("artificial noses") in which the gas is directed over a very large wet surface which results in saturation of the gas with humidity. The "artificial nose" extracts the heat and humidity needed from the patient's expiratory gas. Filter pads e.g. from air conditioning technique get the heat and humidity needed from a water bath or similar device. While heating and humidifying the gas filter pads filtrate it from particles;

(9) Booster Systems (e.g. DE 44 32 907) try to compensate for the insufficient efficiency of an "artificial nose" (HME) by means of adding both fluid and heat which requires a technically demanding control circuitry;

(10) A Combination of the Above Mentioned Systems (e.g. DE 296 12 115) in which first the gas is overheated and humidified. Then in a following second step the gas is cooled down to a target temperature by means of metal lamellas or equivalent. During that step any humidity above saturation will form condensate dripping from the metal lamellas. The condensate is recirculated to the humidifier;

(11) Ambient Air Humidifier with a Stack of Rotating Plates (e.g. DE 37 35 219) systems use a stack of rotating plates which during a part of each rotation dip into water thus becoming wet. A fan drives the gas along those stacks. The idea is that so the gas will be both cleared from any particles, and humidified. Those systems need a non-volatile additive in the fluid to reduce the fluid's surface tension thus allowing for a sufficient wetting of the stack of plates;

(12) Counter-flow Humidfication (e.g. EP 1558877) in which water and gas flow move in opposite directions through a large counterstream exchange surface; and/or

(12) other forms of humidification systems.

As regards preferred humidification concepts reference is made to the above discussion with regard to the prior art as well as to EP 1 558 877 A1 which relates to a specifically preferred humidification method and concept but furthermore provides a summary of further preferred and known humidification concepts, eventually by further reference to further literatures. These contents are incorporated herein by reference An embodiment can consist at least of a control and regulation unit with an interface for the humidifier chamber, wherein various chambers with different technologies or concepts can be used.

In an embodiment the chambers communicate with the humidifier by means of wired or wireless transmission of identification characteristics, so that the control/regulation algorithms, the monitoring and alarm functions, as well as the user interfaces can be adjusted automatically. Alternatively, the adjustment may be manual so that adjustments are made by the user.

In addition to the above-mentioned operational behavior, in certain embodiments parameters that are dependent on the chamber or the application may also be adjusted, e.g. the monitoring of the maximum lifetime of the respective humidifier chamber, but also, e.g., the maximum desired temperature of the heating plate and/or the distribution of priorities in case of an insufficient electrical power in the power supply unit (e.g. prioritizing the heating of the inspiration tube vis-à-vis the heating of the expiration tube in case a secondary battery with counter-flow chamber is used).

In certain embodiments an amplitude- and/or frequency-modulated electromagnet may be integrated into the humidifier that universally realizes the drive for the water movement for various kinds or chamber technologies via magnetic couplings. Thus, it is possible, e.g., to operate counter-flow evaporator chambers and also passover chambers which can optionally be equipped with a magnetically coupled additional movement means (which may comprise several individual movement elements) for the water, so that the temperature gradient between the bottom of the chamber and the surface of the fluid can be reduced if required. In certain embodiments the chambers may be driven by having a semipermeable separating membrane between fluid and gas.

In certain embodiments, the intensity of the water movement can vary, e.g., on the basis of operating parameters (e.g. average gas flow) but also on the basis of adjustments by the user, wherein exclusively electro-mechanical energy is used for the circulation/movement (in contrast to bubble humidifiers in which this is partly realized by means of pneumatic energy).

Thermal energy is transmitted from the humidifier to the humidifier water, e.g., by means of a normal temperature-controlled heating plate on the metallic or plastics-based bottom of the humidifier chamber or also by means of one of the external interfaces for heating elements, e.g., in case the humidification should be realized only close to the patient. In this case the required water can be supplied by a water container with integrated (e.g. magnetically coupled) pump which is slipped on or coupled to the humidifier. Alternatively, the water may be heated, inductively, or by high-energy radiation.

The humidifier chambers may also include integrated sensors and/or insertable sensors for controlling purposes. The device and the humidifier chamber comprise corresponding interfaces for this purpose.

In an embodiment the power supply unit is located in a separate assembly. This allows gravity-relevant weight to be shifted from, e.g., the humidifier position itself downwardly, which can be advantageous, e.g., in mobile applications. Moreover, if the power supply unit is realized in a separate assembly, the size of the actual humidifier can be reduced considerably in order to better use the small space available in the direct vicinity of the patient. In certain embodiments the power supply unit is also identified by the humidifier by means of wired or wireless communication so that the operating behavior can also be adjusted thereto. In an embodiment it is also possible to connect, instead of the power supply unit, a secondary battery also having corresponding identification characteristics.

Since the humidifier knows the specifications of the connected power supply, an overloading/excess heating thereof can be avoided in that the power output of the humidifier is adjusted, limited and/or prioritized automatically, if required. This is preferably achieved by the power management as discussed in WP 2010/028427 of Sep. 7, 2009, the content of which is incorporated herein in its entirety. For example by accepting a relatively long heating period when the device is put into service, it is thus possible to use a power supply unit whose power lies only slightly above the required permanent power and which thus can be smaller and lighter than a more powerful device which outputs this higher power only during the heating period.

Moreover, there are embodiments in which the humidifier comprises at least one interface, preferably three interfaces, for feeding and controlling external components. These interfaces are provided particularly for heated tubes as well as for heatable collars in order to prevent condensation in further parts of the respiration circle in which gas is flowing, e.g. filter, sensors and valves.

There is a further embodiment in which any one of these interfaces is realized such that the output power can be measured by the humidifier so that overloading of the power supply or the control unit itself can be avoided or an adaptive output becomes possible.

Moreover, further interfaces for communication with other medical devices are provided, preferably USB interfaces. In particular control commands can be exchanged via these interfaces so that, e.g., the user interface of the humidifier can be used for operating further systems.

In certain embodiments, in particular the operation of a generator for the gas flow or a gas mixer is intended, but also further configurations are possible, e.g., coupling to a monitoring system for transmitting the patient's temperature to the humidifier or also coupling to respiration devices or respiration therapy devices. In the latter case it is advantageous to use the user interface of the respiration device for remotely controlling the humidifier therewith. In this configuration the operating element of the module of the humidifier is not necessary, so that this configuration differs from the configuration mentioned in DE 10 2006 045 739 B3.

Another and/or additional aspect of the present technology relates to humidifiers for medical gases with a humidifier chamber which can be illuminated with light of a visible wavelength as well as with wavelengths in the UV range for improving the hygienic water quality as well as with wavelengths in the infrared range and suitable detectors for detecting operational states. Also, a respective method of conveying signals is discussed.

An aspect of the present technology is the intelligent further development of technology for reducing the germs present in a humidifier chamber as discussed in more detail below.

An aspect of the present technology is the intelligent further development of technology for performing contactless temperature measurements.

A device according to the certain embodiments comprises at least a control and operating unit (humidifier), a humidifier chamber as well as optionally heated tubes as well as at least one illumination unit or optical interface. Shades of colours and brightness are adjustable (e.g. realization by means of RGB-LEDs), in order to allow an adjustment to the respective operating environment by the user or automatically (bright room/dark room).

In certain embodiments, the illumination unit may also be used for supporting the visual signaling of warnings and alarms, e.g., in that the chamber flashes or glows synchronously with respective warning LEDs in the operating part in a suitable colour.

In certain embodiments the control of the germs inside a humidifier chamber can be improved in that the humidifier and/or the humidifier chamber is/are provided with an UV radiation source which can kill the DNA in bacteria, viruses and protozoa when a suitable wavelength is selected. The prerequisite for an effective sterilization of the water contained in the humidifier chamber is a suitable structural arrangement of the radiation source relative to the humidifier chamber used, in particular with respect to aspects of radiation and, if necessary, aspects of sealing. For protecting patient, user and other persons, there are moreover provided suitable protective measures which reliably prevent them from an undesired exposition to UV light or reduce said exposition to an acceptable level. The UV radiation source can be operated permanently or intermittently. The sterilizing effect of the UV radiation source becomes particularly effective if the water to be sterilized is moved or mixed, as is common in various humidification systems (e.g. counterflow evaporator). The use of UV radiation sources of course requires the selection of suitable materials which are not damaged during their intended service life under the influence of the radiation.

Moreover, in certain embodiments further data of the illumination of the humidifier chamber are collected in a contactless manner by respective sensors on the device by evaluating the light reflection, in particular information about the temperature of the fluid or gas. For example, so-called thermopiles, i.e. infrared thermometers, which can scan the surface temperature optically, may be used.

When using at least partially transparent tubes, an embodiment is conceivable in which also parts of the respective tube can be illuminated alternatively or in addition to the humidifier chamber.

The size, shape, design, selected material and technical concepts of the components mentioned above and described to be used in the examples are not subject to any specific exceptions, so that the selection criteria known in the field of application can be used without restrictions.

Since at least one embodiment is provided in which the humidifier chamber is provided with an encoding element that can be read by the humidifier, the illumination as well as the UV radiation and/or also the contactless detection are adjusted automatically to the respective design of the chamber.

An embodiment may, for example, comprise only one or also more or all of the above-mentioned features and functions, either individually or in combination. Therefore, a large number of alternative embodiments may be realized.

In certain embodiment humidifier chambers having visualization of signals emitted actively by the humidifier are provided for informing and/or warning the user.

The present technology improves the conveyance and noticeability of optical signals. This is particularly supported by amplifying the optical signal by means of the humidification chamber and the liquid contained therein.

Another and/or additional aspect of the present technology relates to a method and device for the temperature-controlled electrical heating of tube assemblies for medical gases (in particular respiration tubes). In particular, this technology relates to a method for safeguarding failure safe functionality and/or for preventing overheating of a heated tube as well as to a respective device and system.

In certain embodiments a method and/or device comprises means for heating tubes for medical gases, in particular respiration tubes, comprising at least a control and operating unit (in the following also referred to as humidifier because it typically also consists of a humidifier module), at least one heating tube with at least one temperature sensor at the end of the respective heating section.

In certain embodiments a method and/or device may detect the presence of a sufficient gas flow in the heated tube. For example, gas-conducting components can be monitored by means of a cyclic variation of (preferably reduction in) the heating power and an evaluation of the temperature response curves so that a heat accumulation in components through which no gas is flowing can be avoided automatically.

In certain embodiments a method and/or device comprises a controller of the heating tube used for the temperature control (typically a component of a respiratory gas humidifier, but in accordance with the technology also a standalone component is possible), wherein the controller always takes one of the three states
"sufficient gas flow",
"insufficient gas flow"
"unknown gas flow"
and controls or reacts as follows in an accordingly adjusted manner:

1. Heating tube controller in the state "sufficient gas flow" or "unknown gas flow":

When outputting a continuously high heating power above a threshold, the power output is intermittently lowered for a short time for evaluating the temperature curve in response to this intentionally caused deflection. The characteristics (interval, time, deflection) of this step can be adjusted or evaluated in accordance with the environmental temperature, and for validating the result, also a plurality of escalating steps can be carried out one after the other until a sufficient gas flow can be clearly detected or excluded on the basis of the interpretation of the sum of the respective temperature responses. When the state "insufficient gas flow" has been detected, the tube heater is switched off or the heating power is reduced to a minimum value until a gas flow can again be detected (see below item 2).

2. Heating tube controller in the state "insufficient gas flow":

When a high heating power is intermittently output for a short time, the temperature response curve is evaluated with respect to this deflection. The characteristics (interval, time, deflection) of this step can be adjusted or evaluated in accordance with the environmental temperature, and for validating the result, also a plurality of escalating steps can be carried out one after the other until a sufficient or insufficient gas flow is clearly detected on the basis of the interpretation of the sum of the respective temperature responses.

If a sufficient gas flow has been detected, the tube heater is activated again (see above item 1).

In this regard it is an important frame condition that the heating power output for the detection must, when being averaged, be so small during a relatively long time period that a relevant heating of the heating tube is excluded (because the very purpose of this detection is avoiding a heat accumulation).

This gas flow detection can also be signaled for the signaling in the user interface of the respective control device.

According to a further embodiment, further reactions of the control device may be adjusted by the user, e.g., the signaling of a warning in case of a gas flow standstill/renewed gas flow and/or the automatic re-activation of a humidifier being in a standby state as soon as a gas flow is detected.

Another and/or additional aspect of the present technology relates to an improved humidification chamber as well as to an improved method for manufacturing such chamber.

In particular, the technology relates to an improved sealing between the metal bottom and plastics parts of humidifier chambers for medical gas humidifiers, in particular for use in methods for treating sleep disordered breathing (SDB) as well as to a method for manufacturing the same. Another aspect relates to welding a lid to the humidification chamber.

In certain embodiment the present technology provides an improved humidification chamber and an improved method for manufacturing the same, wherein particularly the disadvantages of the prior art are to be overcome or at least ameliorated.

In certain embodiments a method and device for carrying out the method includes sealing exclusively by elastically clamping the metallic bottom into a corresponding counterpiece of the plastics part. Thus, no additional sealing component is necessary.

In an embodiment, the sealing is circular. However, also other shapes are possible.

Moreover, in an embodiment the sealing, particularly by respective adaptation of the geometry of the sealing, is realized such that it is self-intensifying when a pressure is applied, i.e. the sealing partners interlock more deeply with one another due to their geometry.

In one embodiment the bottom is thus provided preferably by deep drawing, hydro-shaping or similar methods with a three-dimensional geometry which has a bead. In addition, the bottom is adapted such that it contacts the wall of the plastics part, which essentially corresponds to an inner cylinder in the area of the sealing, in a suitable angle and/or in the unloaded state has a larger diameter than the inner cylinder, which is essentially reduced, preferably elastically, during injection.

For improving the sealing quality after pressing, it is preferred to apply a substantial overpressure to the humidifier chamber for a short time, particularly in order to cause the self-sealing process to continue.

In certain embodiments, a mechanical lock can be provided below the bottom, particularly in order to prevent the bottom from being pressed out when the pressure in the chamber is too high.

An embodiment may, for example, comprise only one or also more or all of the features and functions described herein, either individually or in combination. Therefore, a large number of alternative embodiments may be realized.

The present technology moreover relates to one or more of the following aspects:

1. Humidifier for humidifying medical gases, comprising a humidification module including a control unit, wherein the humidification module is adapted for receiving a humidification chamber, and wherein the humidification module is further adapted to sense and/or receive information on a connected humidification chamber and/or additional equipment such as hoses, power supply pack.
2. Humidifier according to any one of the preceding aspects further including a humidification chamber coupled to the humidification module.
3. Humidifier according to any one of the preceding aspects, wherein the different kinds of humidification chambers differ by their humidification concept.
4. Humidifier according to aspect 3, wherein the humidification concepts include pass-over humidification, counter-flow humidification, humidification by fluid contact by means of membranes, flash evaporation, bubble humidification and/or wick evaporation wherein these and/or additional concepts preferably include concepts where liquid, such as water, and/or gas, such as air, is moved.
5. Humidifier according to any one of the preceding aspects, wherein the humidification module comprises an interface for mechanically and/or operationally coupling with different kinds of humidification chambers.
6. Humidifier according to any one of the preceding aspects, wherein the humidification module comprises sensing means for sensing the kind of humidification chamber connected therewith.
7. Humidifier according to any one of the preceding aspects, wherein the control unit comprises different kinds of operating modes and/or operating algorithms, each operating mode being adapted to specifically operate a humidification chamber.
8. Humidifier according to any one of the preceding aspects, being adapted to be coupled to different humidification chambers of different kinds and wherein, preferably, the humidifier is adapted to operate in an operation mode and/or operating algorithm depending on the kind of and/or on the specific humidification chamber coupled to the humidifier module.
9. Humidifier according to any one of the preceding aspects, wherein the humidifier, preferably the control unit, is configured to adapt and/or select an operating mode and/or control algorithm for humidification depending on the sensed humidification chamber.
10. Humidifier according to any one of the preceding aspects, wherein the interface operates by means of mechanical, wired, and/or wireless transmission of information, such information preferably including identification information and/or operation information.
11. Humidifier according to any one of the preceding aspects, wherein the humidification module comprises interfaces for sensing or exchanging information with a connected humidification chamber, the interfaces including one or more of mechanical interface, wired interface including electrical interface, magnetic interface, wireless interface including optical interface such as infra-red interface, radio interface and the like.
12. Humidifier according to any one of the preceding aspects, wherein the humidifier comprises a connection for an external power supply unit or an external battery.
13. Humidifier according to any one of the preceding aspects, wherein the humidifier is adapted to operate additional equipment such as respiratory hoses and/or heating sheath.
14. Humidifier according to any one of the preceding aspects, wherein the humidification chamber comprises identification features allowing identification of the specific kind of humidification chamber and/or the specific humidification chamber by the humidifier, preferably by means of one or more of the interfaces provided on the humidification module.
15. Humidifier according to any one of the preceding aspects, wherein the humidification chamber comprises identification features such as demand- or power-associated identification features, preferably sensed via the humidification chamber's power demand.
16. Humidifier according to any one of the preceding aspects, wherein the humidifier is adapted to automatically recognize the connected humidification chamber, preferably on the basis of identification features being unique for each kind of humidification chamber and/or humidification concept; and/or on the basis of user input data; and to select and/or adapt the operation mode and/or operation algorithm accordingly.
17. Humidifier according to any one of the preceding aspects, wherein an operating mode and/or control algorithm for humidification includes parameters being dependent on the kind and/or individual humidification chamber and/or on the individual application, which can be adjusted, such parameters including the monitoring of the maximum lifetime of the individual humidification chamber, the maximum temperature of the heating plate and/or the allocation of priorities, preferably in case of an insufficient electrical power supply.
18. Humidifier according to any one of the preceding aspects, wherein an operating mode and/or control algorithm for humidification includes an allocation of priorities, such as prioritizing heating of an inspiration tube vis-à-vis heating of an expiration tube in case the power supply does not allow parallel heating of both tubes to the desired extent.
19. Humidifier according to any one of the preceding aspects, wherein the humidification chamber includes an amplitude- and/or frequency-modulated electromagnet for driving a fluid movement device, such as an rotor, of different humidification chambers, preferably of different humidification concepts, such as passover-chambers, counterflow-chambers, and/or chambers with a semi-permeable separating membrane between fluid and gas.
20. Humidifier according to any one of the preceding aspects, wherein the humidification module comprises means for heating water such as a heating plate, induction heating means and/or radiation heating means and/or wherein the humidification module is adapted to connect to and control a heating means arranged downstream of the gas flow and close to the patient.
21. Humidifier according to any one of the preceding aspects, wherein the humidification module comprises connections for connecting to sensors provided in and/or on the humidification chamber and/or wherein the humidification module comprises sensors adapted to be connected to the humidification chamber comprising respective connections.
22. Humidifier according to any one of the preceding aspects, comprising a power supply unit being separate and external from the humidification module, wherein, preferably, the humidifier is adapted to sense a power supply unit or a battery, preferably by means of wired or wireless communication of identification characteristics.
23. Humidifier according to any one of the preceding aspects, wherein an operating mode and/or control algorithm for humidification includes alarm and/or failure prevention functions, depending on the individual humidification chamber connected to the humidification module, including overload and/or excess heating prevention by means of power output adjust, limitation and/or prioritization.
24. Humidifier according to any one of the preceding aspects, wherein the humidification module comprises a plurality of interfaces for feeding and/or controlling external components, such as heated tubes, heated collars or sheaths.
25. Humidifier according to aspect 24, wherein the humidifier is adapted to individually measure the power consumption or output power for each of the interfaces, preferably allowing an adapted power output and/or overloading of the power supply or control module.
26. Humidifier according to any one of the preceding aspects, wherein the humidifier comprises interfaces for communication with other medical devices wherein the humidifier is preferably adapted to control and operate such other medical devices, preferably including monitoring systems and blowers.
27. Humidifier according to any one of the preceding aspects, comprising a humidification chamber, preferably as referred to in any one of the preceding aspects.
28. Humidification chamber including information on the individual kind of humidification system applied and being adapted to allow humidifier, preferably according to any one of the preceding aspects, to sense or receive said information.
29. Humidification chamber according to aspect 28, preferably further according to the humidification chamber as referred to in any one of the preceding aspects.
30. Humidifier set comprising a humidifier, preferably according to any one of the preceding aspects, as well as at least two humidification chambers, preferably as referred to in any one of the preceding aspects, and preferably being of different kinds and/or humidification concepts.
31. Method for adapting operation of a humidifier, including sensing of identification features of a humidification chamber by a humidifier comprising a humidification module and a humidification control unit, and choosing and/or adapting, preferably automatically, an operating mode and/or control algorithm for humidification depending on the sensed information.
32. Humidifier for humidifying medical gases, preferably according to or in combination with any of the preceding aspects, comprising a humidification module including a control unit, wherein the humidification module is adapted for receiving a humidification chamber, and wherein the humidification module comprises an optical interface for sensing and/or conveying information, the optical interface being arranged to be directed to the humidification chamber such that the humidification chamber is illuminated.
33. Humidifier according to preceding aspect 32 further comprising a humidification chamber coupled to the humidification module.
34. Humidifier according to any one of the preceding aspects 32-33 wherein the optical information provided comprises information on operating parameters, operating conditions, and/or alarms.
35. Humidifier according to any one of the preceding aspects 32-34 wherein the humidification module is further adapted to sense and/or receive information on a connected humidification chamber and/or additional equipment such as hoses, power supply pack and wherein the signals emitted by the optical interface are aligned with the specific humidification chamber and/or humidification concept used.
36. Humidifier according to any one of the preceding aspects 32-35 wherein the optical information is associated with colours, intensity, and/or light or illumination patterns, such as blinking patterns.
37. Humidifier according to any one of the preceding aspects 32-36 wherein a first colour is used to indicate an error and a second colour is used to indicate correct functioning.
38. Humidifier according to aspect 37 wherein the first colour is red and/or the second colour is green.
39. Humidifier according to any one of aspects 32-36 wherein the device in adapted to allow the customer to set the colour, intensity and/or illumination pattern for the illumination.
40. Humidifier according to any one of aspects 32-39 wherein the illumination pattern and/or intensities are preset.
41. Method for operating a humidifier, preferably a humidifier according to any one of aspects 32 to 40, wherein information is sensed and/or conveyed by an optical interface such that the humidification chamber is illuminated.
42. A method, preferably in combination with the any one of the preceding aspects, for preventing overheating and controlling gas flow in a heated tube, the method comprising the steps of
operating a gas flow heating so as to induce a predefined temperature profile to the gas flow;
measuring the characteristics of the temperature response to said change in heating; evaluating the temperature response characteristic; and
initiating a predefined operation, such an alarm or repetition of said process after a certain, preferably predefined, time on the basis of said evaluation.
43. Method according to aspect 42, wherein the temperature sensor is preferably arranged at the patient's end of an inspiration tube
44. Method according to any one of aspects 42-43, wherein inducing the temperature profile is achieved by cyclic variation of the heating power.
45. Method according to any one of the preceding aspects 42-44, wherein the temperature profile includes a raise and or fall of temperature.

46. Method according to any one of the preceding aspects 42-45, wherein the method is performed automatically.
47. Method according to any one of aspects 42-46, wherein including the step of evaluating whether there is "sufficient gas flow", "insufficient gas flow", or "unknown gas flow".
48. Method according to any one of aspects 42-47, wherein a state "sufficient gas flow" or "unknown gas flow" is detected by outputting a heating power above a predefined threshold, intermittently lowering the power output for a short time, evaluating the temperature curve in response to this intentionally caused lowering of the power output.
49. Method according to aspect 48, wherein the characteristics such as interval, time, and/or deflection are adjusted and/or evaluated in accordance with the ambient temperature.
50. Method according to any one of aspects 42-49, wherein a plurality of escalating steps is carried out one after the other until a sufficient gas flow can be clearly detected or excluded on the basis of the interpretation of the sum of the respective temperature responses.
51. Method according to any one of aspects 42-50, wherein, when the state "insufficient gas flow" is detected, the tube heater is switched off or the heating power is reduced to a minimum value until a gas flow can again be detected.
52. Method according to any one of aspects 42-51, wherein when a state "insufficient gas flow" is detected, a high heating power is intermittently output for a short time, the temperature response curve is evaluated with respect to this deflection.
53. Method according aspect 52, wherein the characteristics such as interval, time, and/or deflection are adjusted and/or evaluated in accordance with the ambient temperature.
54. Method according to any one of aspects 42-53, wherein if a sufficient gas flow is detected after an insufficient gas flow and/or an unknown gas flow, the heater is activated again.
55. Method according to any one of aspects 42-54, wherein the heating power output for the detection is, when being averaged over a certain time period, so small during that a relevant heating of the heating tube is excluded.
56. Control unit for controlling a heating of a heated tube, preferably a heated tube for providing breathable gas to a patient, adapted to perform a method according to any one of aspects 42-55.
57. Control unit of aspect 56, being connected to or comprising a breathing tube and a heater for such tube, the tube comprising a temperature sensor at the end of a respective heating section of the heated tube.
58. Blower for providing breathable gas to a patient, the blower comprising a control unit according to aspects 56 or 57.
59. Humidifier for humidifying breathable gas to be supplied to a patient, preferably according to any one of the preceding aspects, the humidifier comprising a control unit according to aspects 56 or 57.
60. Device according to one of aspects 56 to 59, wherein the tube and/or the device does not comprise a flow sensor.
61. Method or Device according to any one of the preceding aspects, wherein the status is visualized, preferably optically and/or acoustically, wherein the status may be the status of evaluation, such as "sufficient gas flow", "insufficient gas flow", or "unknown gas flow" or the status of the device such as "no gas flow→standby/no heating" and/or "gas flow→heating".
62. A method of producing a humidifier chamber comprising the following steps:
   providing a humidifier chamber component made of a first material;
   providing a humidifier chamber bottom made of a second material;
   pressing the humidifier chamber bottom into the humidifier chamber component;
   heating the humidifier chamber bottom.
63. A method according to aspect 62, wherein the first material is plastics, preferably a thermoplastic resin.
64. A method according to any one of aspects 62-63, wherein the second material is a metal, preferably aluminium or tin plate.
65. The method according to any one of aspects 62-64, wherein the first and second materials are biocompatible.
66. The method according to any one of aspects 62-65, wherein the humidifier chamber component comprises a circumferential humidifier chamber wall and/or a humidifier chamber bottom opening for receiving the humidifier chamber bottom.
67. The method according to any one of aspects 62-66, wherein the humidifier chamber component and the humidifier chamber bottom are formed such that they may be press-fit into the humidifier chamber component, in particular the humidifier chamber bottom opening.
68. The method according to any one of aspects 62-67, wherein the humidifier chamber component and/or the humidifier chamber bottom opening has/have a round, preferably circular cross-section, preferably in the form of an inner cylinder, and/or wherein the humidifier chamber bottom is round, preferably circular.
69. The method according to any one of preceding aspects 62-68, wherein clamping and heating leads to a sealing connection between the humidifier chamber component and the humidifier chamber bottom.
70. The method according to aspect 69, wherein the sealing is fluid tight, in particular liquid tight.
71. The method according to aspect 69 or 70, wherein the sealing effect is exclusively achieved by elastically clamping the humidifier chamber bottom into the humidifier chamber component.
72. The method according to any one of aspects 62-71, wherein no additional sealing component and/or material is used.
73. The method according to any one of aspects 62-72, wherein the geometry of the sealing is such that it is self-supporting under pressure load.
74. The method according to any one of aspects 62-73, wherein the geometry of the humidifier chamber bottom, in particular in the area of a humidifier chamber bottom edge exercising a sealing effect together with the humidifier chamber component, is selected such that a pressure load from the humidifier chamber inside effects a radial, outwardly directed movement and/or force of the humidifier chamber bottom, preferably directed towards the humidifier chamber component.
75. The method according to any one of aspects 62-74, wherein the humidifier chamber bottom comprises a preferably circumferential crimp.
76. The method according to any one of aspects 62-75, wherein the humidifier chamber bottom is formed, preferably by deep-drawing, hydroforming or similar methods, such that it touches the humidifier chamber component at a suitable angle and/or, if unloaded, has a greater diameter than the humidifier chamber component or the humidifier chamber bottom opening, which diameter is reduced, preferably essentially elastically, during pressing.

77. The method according to any one of aspects 62-76, wherein heating upon pressing is effected without impact on the humidifier chamber component and/or humidifier chamber bottom.

78. The method according to any one of aspects 62-77, wherein upon pressing and heating positive pressure is applied to the humidifier chamber, preferably for approximately 5 to 60 s, particularly preferably for approximately 10 to 40 s, and preferably amounting to approximately 300 to 500 mbar, particularly preferably 350 to 450 mbar, moreover preferably approximately 400 mbar.

79. The method according to any one of aspects 62-78, wherein the humidifier chamber component underneath the bottom is provided with a mechanical lock so as to particularly avoid disassembly when the chamber pressure is excessive.

80. A humidifier chamber comprising a humidifier chamber component made of a first material and a humidifier chamber bottom made of a second material, wherein the humidifier chamber bottom and the humidifier chamber component are in direct and tight contact.

81. The humidifier chamber according to aspect 80, wherein the first material is plastics, preferably a thermoplastic resin.

82. The humidifier chamber according to aspect 80 or 81, wherein the second material is a metal, preferably aluminium or tin plate.

83. The humidifier chamber according to any one of the preceding aspects 80-82, wherein the first and second materials are biocompatible.

84. The humidifier chamber according to any one of aspects 80-83, wherein the humidifier chamber component has a circumferential humidifier chamber wall and/or forms a humidifier chamber bottom opening for receiving the humidifier chamber bottom.

85. The humidifier chamber according to any one of aspects 80-84, wherein the humidifier chamber component and the humidifier chamber bottom are formed such that the humidifier chamber bottom is press-fit into the humidifier chamber component, in particular the humidifier chamber bottom opening.

86. The humidifier chamber according to any one of aspects 80-85, wherein the humidifier chamber component and/or the humidifier chamber bottom opening has/have a round, preferably circular, cross-section, preferably in the form of an inner cylinder, and/or the humidifier chamber bottom is round, preferably circular.

87. The humidifier chamber according to any one of aspects 80-86, wherein the sealing effect between humidifier chamber component and housing and humidifier chamber bottom is achieved by clamping and heating.

88. The humidifier chamber according to any one of aspects 80-87, wherein the sealing is fluid tight, in particular liquid tight.

89. The humidifier chamber according to any one of aspects 80-88, wherein the sealing effect is exclusively achieved by elastically clamping the humidifier chamber bottom into the humidifier chamber component.

90. The humidifier chamber according to any one of aspects 80-89, wherein no additional sealing component is used.

91. The humidifier chamber according to any one of aspects 80-90, wherein the geometry of the sealing is such that it is self-energising under pressure load.

92. The humidifier chamber according to any one of aspects 80-91, wherein the geometry of the humidifier chamber bottom, in particular in the area of a humidifier chamber bottom edge which has a sealing effect together with the humidifier chamber component, is designed such that a pressure load from the humidifier chamber inside effects a radial and/or outwardly directed movement and/or force of the humidifier chamber bottom, preferably directed towards the humidifier chamber component.

93. The humidifier chamber according to any one of aspects 80-92, wherein the humidifier chamber bottom comprises a preferably circumferential crimp.

94. The humidifier chamber according to any one of aspects 80-93, wherein the humidifier chamber bottom is formed, preferably by deep drawing, hydroforming or similar methods, such that it touches the housing component at a suitable angle and/or, if unloaded, has a greater diameter than the humidifier chamber component or the humidifier chamber bottom opening, which diameter is reduced during pressing, preferably essentially elastically.

95. The humidifier chamber according to any one of aspects 80-94, wherein the humidifier chamber component underneath the bottom is provided with a mechanical lock so as to avoid disassembly if the chamber pressure is excessive.

96. The humidifier chamber according to any one of aspects 80-95, wherein, preferably in a cross-sectional view, humidifier chamber bottom 1 comprises a crimp or a corrugation 5 adjacent to an outer edge 3 of humidifier chamber bottom 1, and preferably circumferentially extending around humidifier chamber bottom 1.

97. The humidifier chamber according to any one of aspects 80-96, wherein a crimp 5 comprises a raising portion 20 raising vis-à-vis central bottom portion 3 of humidifier chamber bottom 1 and a lowering crimp portion 24 angled vis-à-vis raising crimp portion 20 while raising crimp portion 20 and lowering crimp portion 24 merged by crimp apex portion 22.

98. The humidifier chamber according to aspect 97, wherein the length and/or height of raising crimp portion 20 is higher than the length and/or height of lowering crimp portion 24.

99. The humidifier chamber according to aspect 97 or 98, wherein lowering crimp portion 24 transmissions to humidifier chamber bottom outer edge 3 at the lower end of lowering crimp portion 24, wherein, preferably, lowering crimp portion 24 at its lower end is outwardly curved, in a cross-sectional preferred view, to extend into or provide outer edge 3.

100. A method of producing a humidifier chamber, preferably according to any one of the preceding aspects, comprising the following steps:
providing a humidifier lid, being made of a non-laser adsorbent material,
providing a humidifier component, preferably having humidifier side walls, being made of a non-laser adsorbent material,
providing a laser adsorbent sheet,
laser welding the humidifier lid to the humidifier component with the laser adsorbent sheet being interposed between them.

101. A method according to aspect 100, wherein the material of the humidifier lid, the humidifier component and/or the laser adsorbent sheet is translucent, preferably transparent.

102. The humidifier chamber according to any one of aspects 28, 29, 80 to 99 or produced by a method according to any one of aspects 62 to 79, 100 or 101, the humidifier chamber being adapted for use in a humidifier according to any one of aspects 1 to 27, 32 to 40 or 59.

The present technology will now be further discussed exemplarily by making reference to the drawings and exemplary embodiments.

Figure 1:
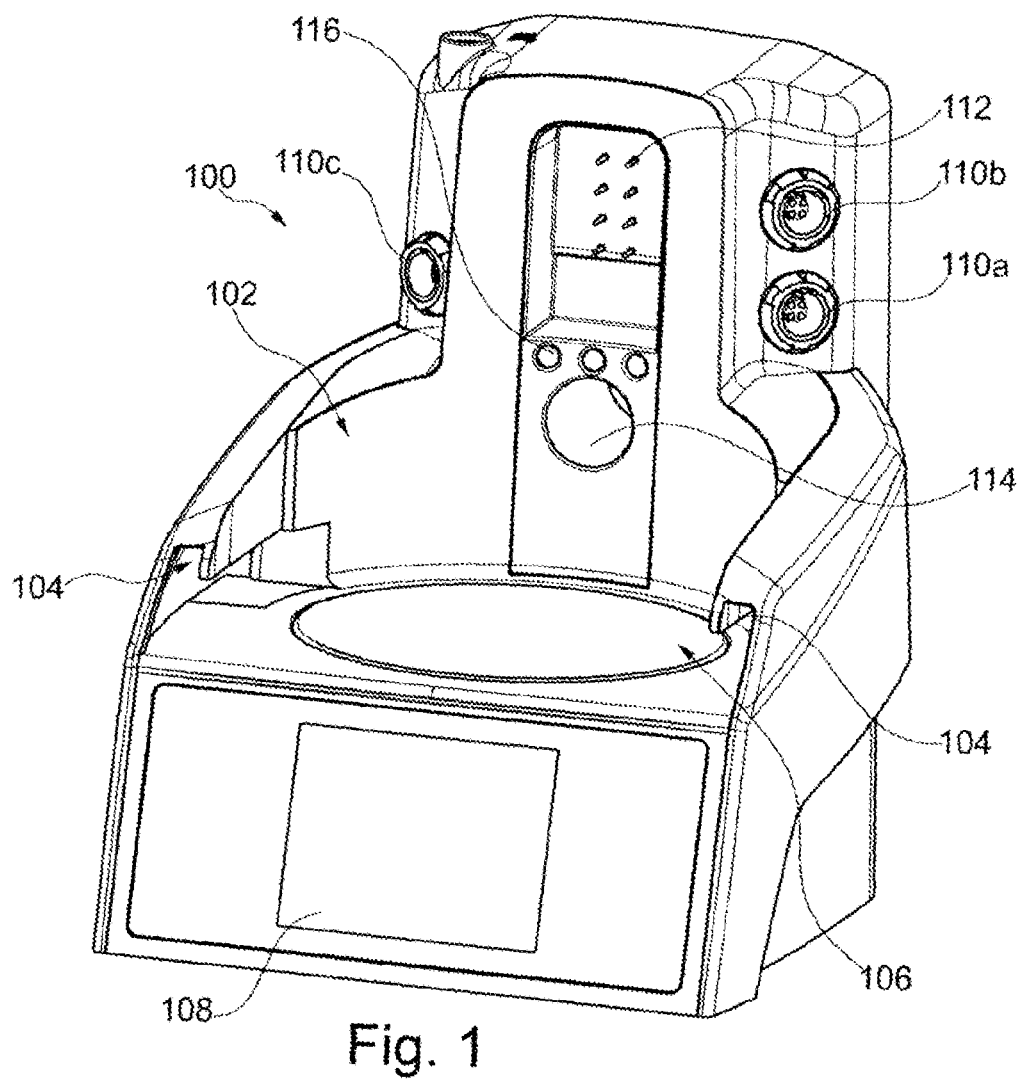
FIG. 1 shows a perspective view of an embodiment of a humidification module.

FIG. 1 shows a humidification module of a humidifier according to the present technology including a control unit (not shown). Humidification module 100 is adapted to receive and operate a humidification chamber for humidifying medical gases, e.g., to be supplied to a patient during medical therapy such as during therapy of sleep disordered breathings. The humidification module 100 may include a humidification chamber receiving portion 102 for engaging with a humidification chamber. The humidification chamber receiving portion 102 preferably includes mechanical locking means, which may exhibit known configurations such as slots, wedges, snap fit engagements and the like, for securing a humidification chamber to the humidification module 100. As will be readily appreciated, humidification module 100 is shown in FIG. 1 and humidification chamber receiving portion 102 may take different visual and geometric appearances as long as it allows to functionally and/or structurally connect to and/or cooperate with a humidification chamber.

Humidification module 100 may include a heating plate 106 for transferring heat from the humidification module to a humidification chamber 120 in order to heat liquid contained therein. Humidification module 100 may further comprise a display and/or user interface 108 for exchanging information with a user. This may be single or bi-directionally, i.e. by providing information to the user, e.g. visually, and/or to allow the user to input information and/or instructions by respective input means, such as buttons, keys or touch screen.

Humidification module 100 moreover comprises a plurality, preferably three or more, interfaces 110a, 110b and 110c for connecting to additional equipment, i.e. additional to the humidification chamber, such as to heated tubes, such as an inspiration tube and an expiration tube as well as to a heatable collar or sheath. Interfaces 110 preferably allow power supply and control of additional equipment such as a heated tube (not shown; see later discussion). It will be appreciated by the skilled person, as is generally known for humidifiers, that air will be provided to the humidification chamber by means of a pressure supply or blower. In the humidification chamber, the air is humidified. This can be achieved by means of different concepts and technologies as further discussed above. Humidified air exits the humidified chamber through a hose leading humidified air for providing humidified air to a patient. Beside such inspiration tube from which a patient may inhale humidified air an expiration tube may be provided through which the patient exhales, which is generally achieved by the provision of valve mechanisms provided in a patient interface and/or blower unit. Additional equipment may include a heatable sheath or the like for tempering additional components of the breathing system such as filters, sensors and valves. Preferred sensors may be temperature, flow, pressure and/or humidity sensor etc. Such heated components increase security by preventing condensation and providing comfort to the patient. Equipment interfaces 110a, 110b, 110c are adapted to provide energy and/or information to the additional equipment and preferably, to receive and/or send information from the equipment connected. This may include, for example, the provision of power for heating energy and/or the sensing of temperature and/or power consumption.

The humidification module 100 moreover comprises interfaces for allowing the exchange of information and/or energy between the humidification module 100 and a humidification chamber connected thereto. Such interfaces may include electrical contacts 112 for providing energy to a humidification chamber and/or for exchanging information with the humidification chamber. For example, sensors provided in or on the humidification chamber may be powered and information sensed may be transferred to the humidification module 100 and the control unit included therein. Additionally and/or alternatively, an amplitude- and/or frequency-modulated electromagnet may be integrated into the humidification module 100 to drive, e.g. via a magnetic coupling, respective drive means of a humidification module. Here, drive interface 114 is provided in a preferably generally cylindrical opening for receiving a corresponding portion of the drive means of a humidification chamber, for example of a water pump. Such interface may be a mechanical drive interface, an electrical drive interface, and/or a respective electromagnet coupling interface. Via such interface, drive means of various kinds of humidification concepts, such as pass-over humidification or counter-flow humidification may be achieved. The same generally applies for humidification concepts using a semi-permeable separating membrane between fluid and gas.

Additionally and/or alternatively, light sensors and/or interfaces 116 may be provided on the humidification module. Such light sensor interfaces may include various functionalities, as will be discussed in more detail separately in the present application with regard to further aspects of the technology. Such functionalities may include conveyance of information, such as operation and/or alarm signals. Such a functionality is preferable advantageously adapted to cooperate with a humidification chamber mounted to the humidification module in a manner such that the signal is amplified and/or scattered in order to increase visibility of the signal and to ensure appropriate conveyance of the desired information. Light sensor interface 116 may also, according to a preferred embodiment include light sensors for sensing reflected light of the humidification chamber.

All interfaces of the humidification module 100, such as electrical interfaces 112, light sensor interfaces 116 and/or magnet interfaces 114 as well as equipment interfaces 110, mechanical humidification chamber receiving interface 104 and/or heating interface 106 may or may not be in communication, particularly controlled, by the humidification module control unit. Preferably, all interfaces of humidification module 100 are controlled by humidification module control units.

In accordance with the present technology, the humidification module and humidification module control unit are adapted to receive and operate or cooperate with different kinds of humidification chambers and/or additional equipment such as hoses etc. Such different kinds of humidification chambers differ by their humidification concept. Various humidification concepts have been discussed and referred to above. Such humidification concepts may include counter-flow humidification, as discussed in more detail and claimed in EP-A-1 558 877 which is herein incorporated by reference, passover humidification, humidification by fluid contact by means of membranes or membrane-type humidification, fiber-type humidification, bubble through humidification, high temperature humidification, ultrasound-type nebulizing humidification, pressure-type nebulization humidification, heat and moisture exchange humidification, filter pad humidification, booster system humidification or a combination of the above mentioned systems as discussed in more detail and incorporated herein by reference in the introductory portion of EP-A-1 558 887.

The humidification module and humidification module control unit includes operating parameters or operating algorithms for operating one or more, preferably all of said kind of humidification concepts as applied by a respective humidification chamber 120 adapted to be coupled, operationally and/or mechanically, to the humidification module 100.

Moreover, the humidification module 100 is adapted to sense the individual specific humidification chamber coupled thereto and/or to sense the kind of humidification chamber connected therewith. Information on the kind of humidification chamber includes information on the general humidification concept applied as well as on the general and/or individual structure of the humidification chamber.

In order to allow appropriate identification of the humidification chamber connected to the humidification module 100, the humidification chamber 120 comprises information on the specific humidification chamber, i.e. a unique information associated with this humidification chamber, information on the specific kind of humidification chamber, i.e. information on a specific series of humidification chamber of a particular manufacturer, and/or information on the humidification concept applied by the humidification chamber. Humidification module 100 and/or humidification chamber 120 (see FIGS. 2A, 3A to be discussed below) are specifically adapted to allow such information to be provided by the humidification chamber, conveyed to and/or sensed by the humidification module.

Humidification module 100, as indicated above, comprises multiple operation modes and/or algorithms associated with the different humidification chambers to be connected to humidification module 100. Humidification module 100 is adapted to apply or run a specific operation mode and/or algorithm on the basis of the sensed humidification chamber.

This may involve, as already indicated above, the appropriate selection of operating parameters such as heating temperature, heating temperature cycles, maximum heating temperature of heating interface 106, driving speed etc. of magnet or drive interface 114, sense of control via electrical interface 112 as well as the respective control and operation of the external additional equipment such as breathing hoses, the heating temperature or cycles etc. The identification information sensed by and/or transmitted to the humidification module may include information on the individual humidification chamber 120 connected to humidification module 100 including information on, e.g., operating hours and service or maintenance cycles of the specific humidification chamber 120.

The information provided on the humidification chamber 120 allowing the humidification module 100 and humidification module control unit to appropriately set and/or apply operational parameters and/or algorithms may be provided by the humidification chamber 120 in different ways. Such may include one or more mechanical keys provided on the humidification chamber 120 sensed by a mechanical sensor or mechanical interface of the humidification module 100 while the humidification module 100 is adapted to sense and distinguish multiple different mechanical keys of the humidification chamber 120 and to appropriately and automatically chose most appropriate operation modes/parameters and/or algorithms. Such mechanical interface (not shown) may be combined with the mechanical fastening interface structure 104 or be separately provided. The information may furthermore be optically stored on humidification chamber, e.g. by means of a bar code or the like, readable by optical interface senses 116 of humidification module 100. Also, the information may be electrically stored, e.g. on a chip provided on the humidification chamber 120, and electrically sensed or read out by electrical interface 112. Additionally and/or alternatively, humidification module control unit may be adapted to start operation of a humidification chamber 120 on the basis of a general operation routine and/or algorithm while the sensors, preferably via the above-discussed interfaces, sense operating parameters such as power consumption, electrical and/or mechanical resistance and the like and adapt or change the applied operating parameters and/or algorithm accordingly.

Preferably, the humidifier according to the present technology comprises an interface (not shown) or connection for an external power supply unit or an external battery or accumulator. Humidification module 100 is preferably adapted to sense information on a power supply unit or battery, preferably by means of wired or wireless communication of operating or identification characteristics, maximum power pack output and/or other operating parameters of the power supply pack or battery. Preferably, the humidification module control unit senses information on the humidification chamber 120 connected to humidification module 100 as well as to the power pack unit or battery (not shown) connected to the humidification module 100 and adapt and/or select the operation modes and/or algorithms based on such information sensed. The operation mode and/or algorithm may include power output adjust, power output limitation and/or power output or supply prioritization, particularly and preferably in order to compensate for insufficient maximum power supply, e.g. due to a power supply pack not providing sufficient power for simultaneous operation of all features of the connected humidification chamber and/or equipment, or in order to save power in a power-saving mode or with battery operation.

As discussed above, this may be of particular advantage in reducing costs and size as well as in improving operability of the humidifier.

As discussed above, such prioritization may be applied during a start or warming-up phase of the humidification module equipped with a counter-flow humidification chamber as well as an inspiration and expiration hose. During the warm-up phase, very high energy consumption is required for heating up the water in the water chamber as well as for heating up the inspiration and expiration hose. Here, a power supply pack or battery may not be able to provide sufficient power for simultaneously fulfilling the required tasks or operations. The automatic sensing and consideration of the power supply pack and humidification chamber as well as equipment, here inspiration and expiration hoses, results in an automatically adapted operation including prioritization of power supply. For example, heating of the expiration hose may be deferred until humidification chamber and inspiration hose have reached the operating temperature. This helps to compensate for power consumption peaks which the power supply unit is not able to or designed to fulfill. In addition, this allows the use of smaller, lighter and/or cheaper power supply units increasing comfort, costs, operability etc.

The operating mode and/or algorithm as applied by the humidifier according to the present technology on the basis of the specific humidification chamber 120 and/or the sensed power supply pack is automatically applied and includes control functions, alarm functions, user input functions (allowing and/or requesting specific user input required for the individual operation on the basis of the connected humidification chamber), power functions, priority control operation functions and the like.

According to a preferred mode of operation, the humidifier module 100 detects, whether it is operated by an accumulator. If this is the case, the following operating parameters are automatically applied. If the target temperature in heated inspiration and/or expiration hoses is not reached, no acoustic and/or visual warning signal will be emitted (contrary to operation with a grid connected power supply unit). Here, it is assumed that no technical malfunction prevails but rather the environment may be cool while the battery does not provide sufficient energy for compensation the cool environment. Also, in order to prevent condensation the water temperature will be lowered automatically to be below the actual temperature of the inspiration hose.

According to a preferred mode of operation, in case the power supply unit does not provide sufficient power, the maximum power the unit can provide is detected. By means of limitation and prioritization of the different users, particularly heating means (heating plate, hose heating, additional heating element) an overload of the power supply pack is prevented. In addition, it is ensured that no condensate will occur in the hoses or tubes.

The present technology is, in line with the above discussion, also directed to a humidifier comprising a humidification module 100, a humidification module control unit as well as a humidification chamber as well as a humidifier set comprising a humidifier, preferably according to anyone of the herein discussed aspects, as well as at least two humidification chambers, preferably as discussed above, while the at least two humidification chambers preferably are of different kinds and/or different humidification concepts. This may be of particular advantage in that it allows the specific adjustment of therapy by simple exchange of the humidification chamber which may involve a change of the humidification concept, thereby taking into account specific needs of the patient, as regards for example comfort level or the like and/or specific requirements of therapy in order to achieve best compliance.

The present technology also relates to an advantageous method for, preferably automatic, adaptation of operation of the humidifier. Such method includes provision of a humidifier as referred to above as well as of at least one humidification chamber as referred to above and to, preferably automatically, choosing and/or adapting an operating mode and/or control algorithm for humidification depending on the sensed kind of humidification chamber and/or power supply unit.

According to a preferred embodiment, the humidifier of the present technology comprises a further interface, for example a USB interface, allowing to upload or change the settings of the humidifier, such as the of the different operating parameters and/or control algorithms stored, preferably on a storage device, of the humidifier module control unit. This allows an improved decent updating of the humidifier keeping it up-to-date with changes to the operation requirements of different humidification chambers and the like as referred to above.

Figure 2A:
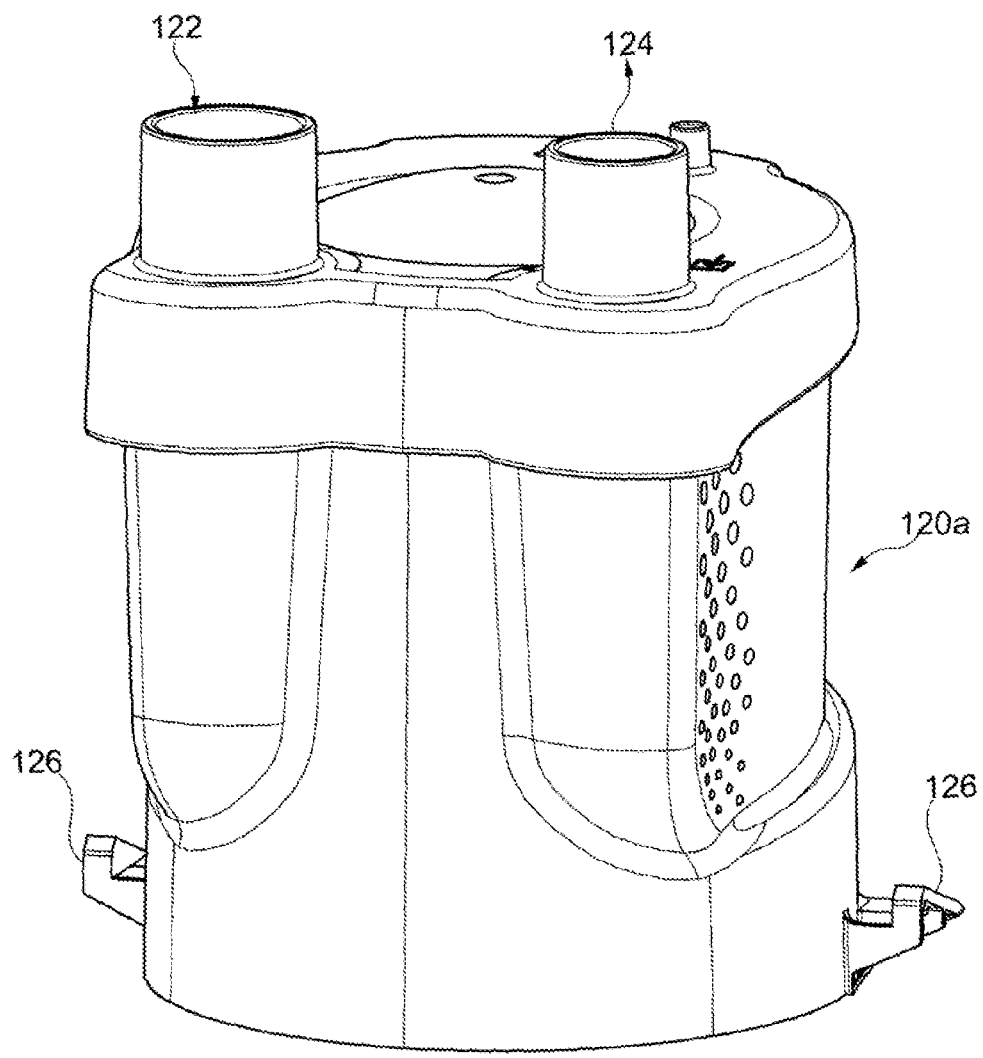
FIG. 2A shows a perspective view of an embodiment of a humidification chamber.
Figure 2B:
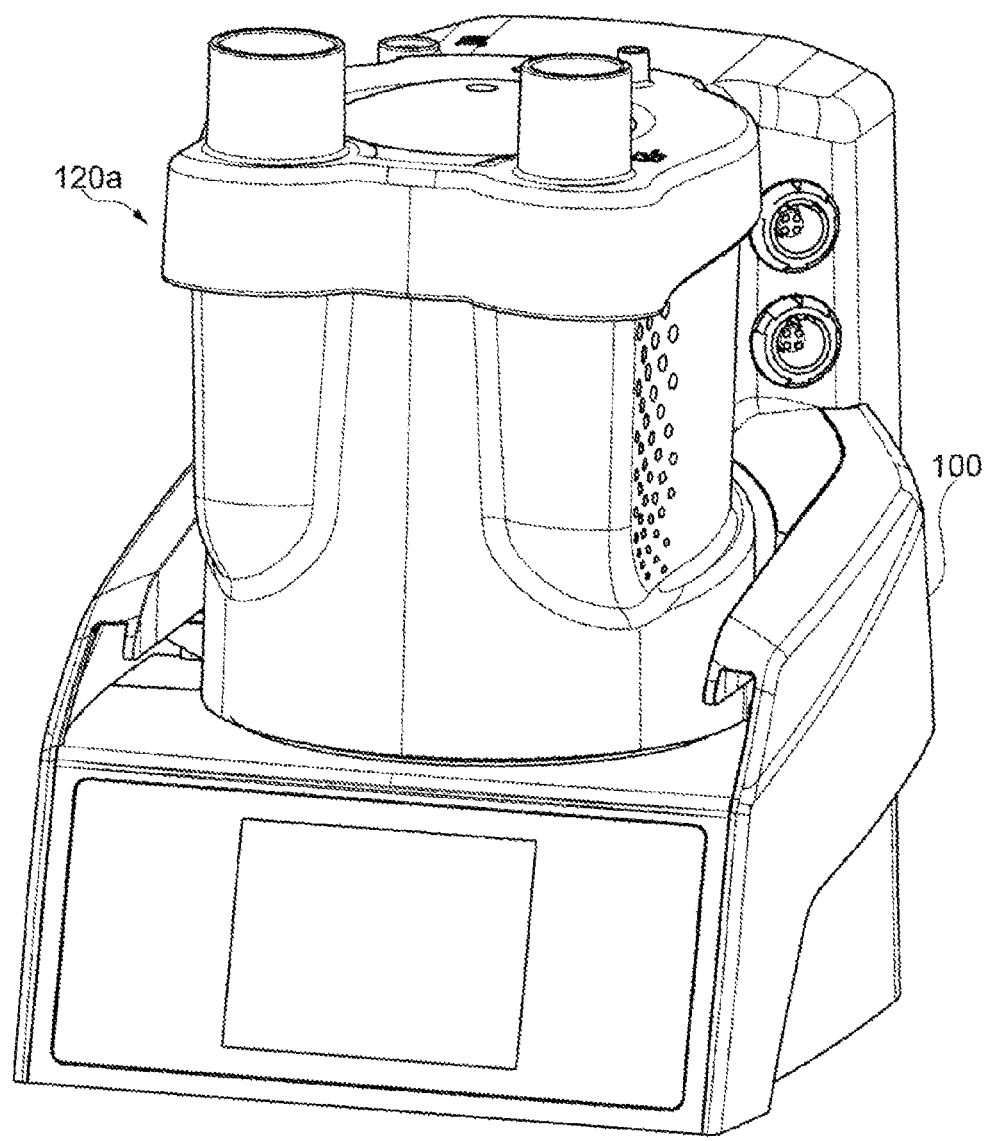
FIG. 2B shows a perspective view of the humidification module of FIG. 1 being equipped with a humidification chamber as shown in FIG. 2A.
Figure 3A:
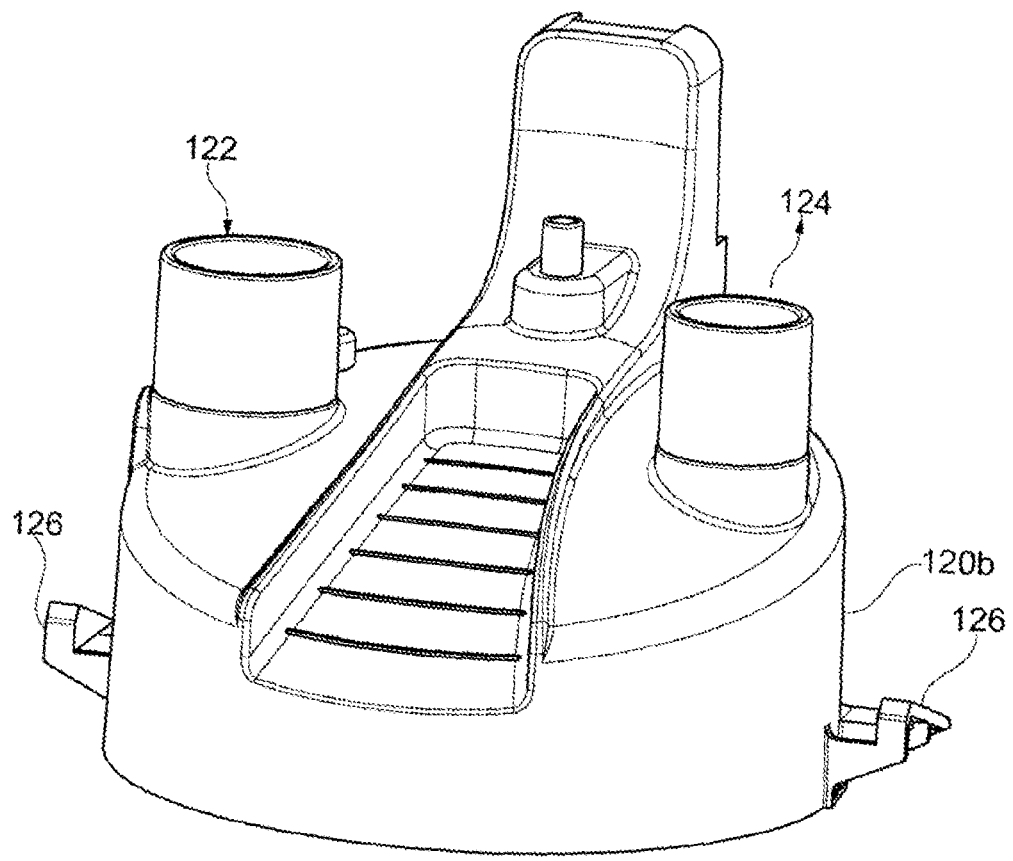
FIG. 3A shows a perspective view of another embodiment of a humidification chamber differing in kind and/or concept from the one shown in FIG. 2A.
Figure 3B:
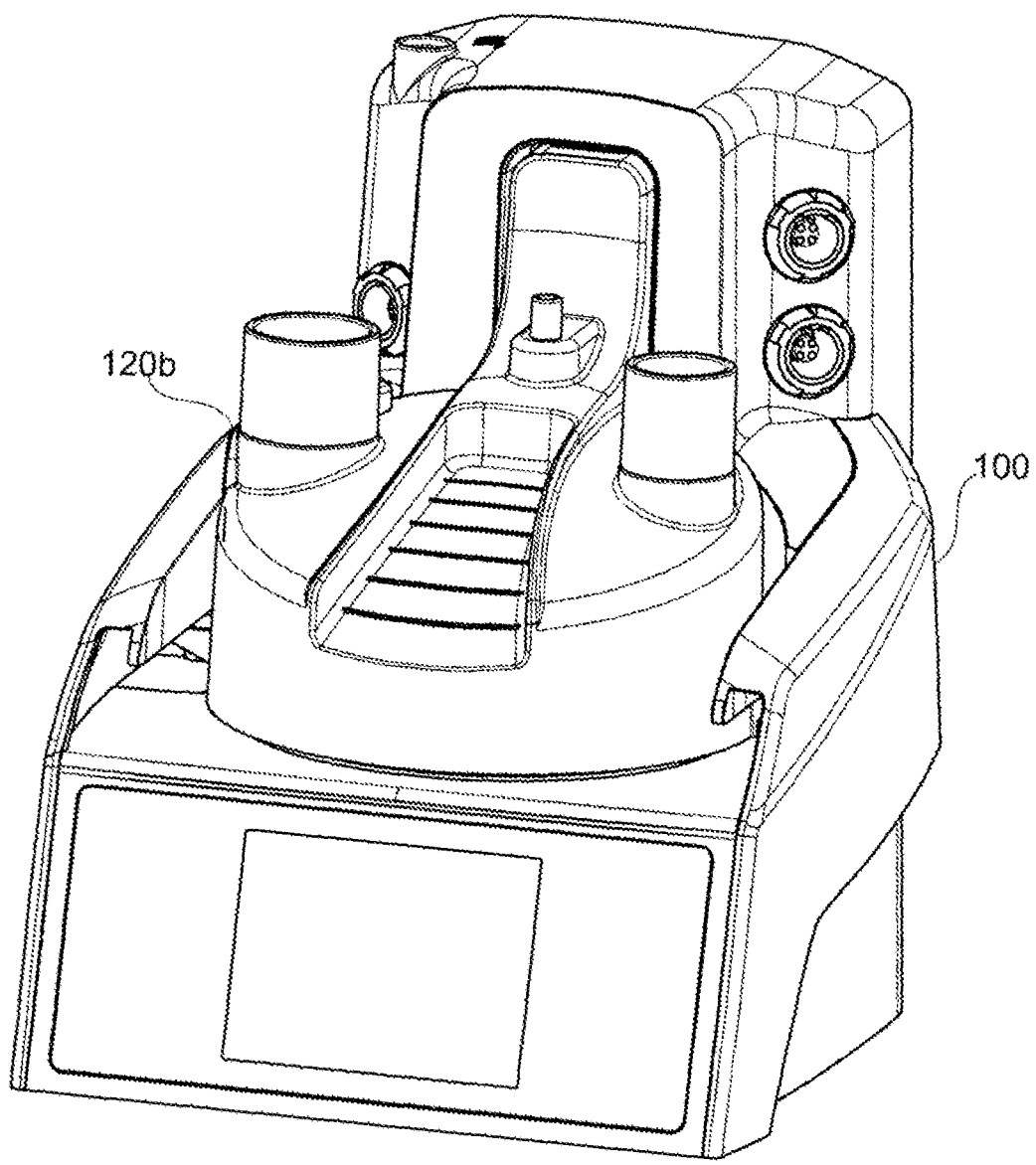
FIG. 3B shows a perspective view of the humidification module of FIG. 1 being equipped with a humidification chamber as shown in FIG. 3A.

FIG. 2A shows a perspective view of a preferred humidification chamber 120a, here a humidification chamber applying the so-called counter-flow humidification as referred to above. The humidifier includes a gas inlet 122 and a gas outlet 124 to be connected to respective hoses from a blower unit (not shown) and to a patient interface (not shown). Humidification chamber 120a furthermore comprises interfaces corresponding to those of humidification module 100 and is further discussed in more detail in the present application (not shown). Such interfaces include mechanical interfaces 126 for positioning and/or connecting and/or providing information on the modification chamber 120a with/to the humidification module 100. Humidification chamber 120a furthermore includes senses (not shown) and interfaces for cooperating with electric interface 112, optical interface 116 and/or mechanical/magnetic/drive interface 114, and/or heating interface 106 of humidifier 100. FIG. 2B shows humidification chamber 120a being connected to humidification module 100. FIG. 3A shows a different humidification chamber 120b applying, according to the preferred embodiment shown here, a different humidification concept, namely a pass-over humidification as further discussed above. Humidification chamber 120b corresponds, as regards to the provision of interfaces to the information provided to humidification chamber 120a as discussed above. FIG. 3B shows a humidification chamber 120b connected to humidification module 100. Humidification module 100 is, as discussed in more detail in the present application, adapted to automatically detect the specific kind of humidification chamber connected therewith and to appropriately adapt and/or chose operating modes and/or parameters.

It is referred to the above discussion of the universal humidifier, while particular reference is made to FIG. 1 showing the perspective view of a preferred humidification module.

As can be seen in said FIG. 1, optical interface 116 is arranged such that it is directed towards the humidification chamber to be connected to humidification module 100 (see, e.g., FIGS. 2B and 3B). Light emitted from optical interface 116 thus illuminates humidification chamber 120, which is adapted to be illuminated and which is preferably semitransparent or transparent. It will be readily understood that humidification chamber 120 does not necessarily have to be fully transparent although this may be of particular advantage but that, for example a translucent humidification chamber may be of particular advantage and suitability for being illuminated.

Light emitted from the optical interface 116 may thus be refracted, spread and/or enforced. In particular, the housing of humidification chamber 120 as well as the liquid, such as water, contained therein contributes in breaking and spreading of the light received from the optical interface 116. This results in the humidification chamber being more or less fully illuminated thus providing an increased glowing or lightning surface. This may particularly increase visuability and noticeability of the information provided by optical interface 116.

In line with the above discussed concept of the universal humidifier, which equally applies to this aspect of the technology, humidification module 100 may advantageously have sensed the humidification chamber connected thereto and provide optical signals through optical interface 116 which are specifically adapted to the particular humidification chamber 120 connected to humidification module 100. Such adaptation may include light colour, light intensity, and light direction. This may particularly be achieved by the provision of respective light sources of different kinds and suitability, such as single colour or multi colour, such as RGB-, LEDs which may be provided at different positions (compare exemplary embodiment shown in FIG. 1). Apparently, also further parameters of the optical interface 116 may be altered to best harmonize with the specific humidification chamber 120 connected to humidification module 100. For example, information conveyance of the information provided by optical interface 116 may be improved by adapting the light emitted to this specific colour of the, preferably translucent, humidification chamber 120. Also, for example, the position from where light is emitted by optical interface 116 and/or the direction of the light emitted may be altered to harmonize with the specific geometric structure of the particular humidification chamber being illuminated. This may result in improved illumination of the humidification chamber and thus in improved information conveyance and noticeability.

The effect of the illuminated chamber being glowing or flashing due to the optical signals provided and induced by optical interface 116 may particularly be enhanced by means of a suitable construction of the humidification chamber and may, additionally or alternatively depend on the humidification concept applied. For example, for counter-flow humidification or other humidification concepts where liquid is moved, an improved visuability is achieved, particularly due to the changing reflections of the optical interface due to the moving liquid. Such dynamic illumination is of particular advantage since it is particularly suitable to attract a user's attention. Similar effects may be achieved by already dynamically emitting light from the optical interface 116.

Optical interface may be or comprise an optical sensor for sensing light signals which may be processed by the control unit.

The information conveyed may include information on the operating parameters such as warm-up phase, operating temperature, operating mode, etc. In addition, the present technology advantageously allows the communication of alarm signals indicating, for example, lack of energy, lack of humidification liquid, overheating and the like.

Preferably, the respective information is conveyed using colour or colour intensity codes as well as signal rhythms. Preferably, green light is applied to indicate working correctly and at temperature. Amber light may be applied to indicate warming up. Red light may be used to indicate an error or any combinations of coloured lights as desired. Flashing or blinking light, such as a flashing or blinking red light, may be used for an error message. In certain embodiments the colour of the light may reduce as the humidifier comes up to temperature, users may not want bright lights continuously, so initially bright and then fades once correct temperature reached. However, any combination of lights or light rhythms may be utlised. According to a preferred aspect, the device in adapted to allow the user to set the colour and/or colour intensity for the illumination, e.g., from a preset pallete of 2-30 different colours, such as 20 colours in, e.g., blue/green/ white colours. According to a preferred aspect, the colour does not change during ordinary operation but only in case of alarms. Alarm signals may distinguish between mid priority alarm (e.g. visualized by flashing in maximum intensity with, preferably the user-set, colour), high priority alarm (e.g. visualized by flashing in red). Both alarms may be synchronized with a, e.g., yellow/red, alarm LED on the device. In certain embodiments the colour illumination may comprise a combination of some user set colours, colour patterns or intensities and some preset colours or colour patterns or intensities.

According to a preferred embodiment, optical interface 116 comprises light sensors which may sense light reflections from specific light signals previously emitted from the light sensor while humidification module control unit is adapted to evaluate, on the basis of the signals sensed, information on filling level of the humidification liquid and/or temperature of the humidification liquid.

In certain embodiments of the present technology overheating of a heated tube is prevented, e.g., in the field of artificial ventilation and/or Continuous Positive Airway Pressure (CPAP) therapy of sleep disorder breathing. Here, the present technology particularly provides a non-therapeutic control and failure prevention algorithm (method and device) which is preferably not related to the therapy per se.

One preferred aspect of this technology is to base the conclusion on whether gas flow through the tube exists or not on the characteristic of a temperature measured in response to a, preferably rapid, change of the heating power. The temperature is preferably measured by a temperature sensor behind the tube heating zone, when seen in the flow direction of gas flow. To achieve this, the temperature sensor is preferably arranged at the patient's end of an inspiration tube while the blower, humidifier and/or a control unit is adapted to apply a respective temperature change pattern, to measure the characteristics of the temperature response to said change in heating power, to evaluate the temperature response characteristic, and to start a predefined operation, such an alarm or repetition of said process after a certain, preferably predefined, time on the basis of said evaluation.

In praxis, heating of the tube is preferably interrupted for conducting the heat measurement by means of the temperature sensor. However, preferably such interruption in heating for conducting the temperature measurement only lasts a few milliseconds and has a negligible influence on the temperature of the breathing hose. Such very short interruption of the heating while taking the temperature measurement is of particular advantage for the accuracy of the temperature measurement and measurement decoupling. Such time for taking a temperature measurement while interrupting hose heating last for well less than about 100 msec, preferably below about 10 msec.

Figure 4:
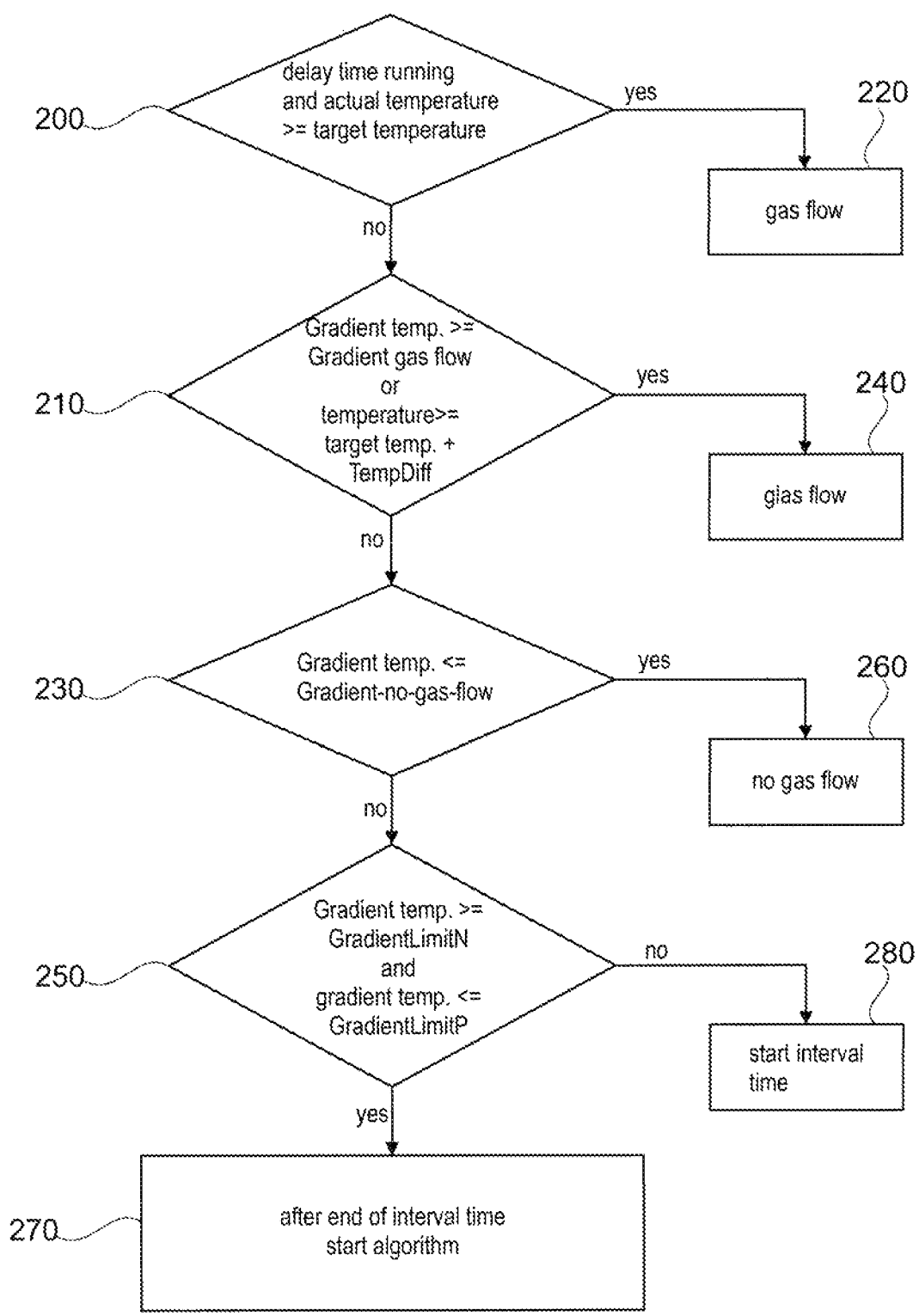
FIG. 4 shows a preferred flowchart of a control routine according to an embodiment of the present technology.

Preferably, such algorithm is applied only for systems running in a steady state. Said algorithm may include additional steps, particularly for assuring that the system runs in a steady state and for considering standard situations in which the existence or non-existence of gas flow can be assumed with high probability. Such preferred control algorithm is shown in a flow chart in FIG. 4.

Such control algorithm starts when the system or the method is started, e.g., when gas should start flowing and the tube heating is turned on. As will be easily understood, during a warm-up time the desired operating parameters are not yet met. Therefore, the algorithm foresees a certain delay-time, preferably starting when the system is turned on. During such delay time the predefined heating pattern for evaluating existence or non-existence of gas flow is not applied. Particularly, the unsteady system is preferably assumed not to allow reliable conclusions. However, during the running of such delay time, which preferably lasts for about 15 sec to 20 sec, preferably for about 30 to 60 seconds. in step 200, the control unit performs a temperature measurement and evaluates whether the actual temperature is larger or equal to the target temperature which is to be expected on the basis of the heating power applied. If this holds true, gas flow is assumed (see step 220). Here, it is to be understood that even if actually no gas flow exists, the actual temperature being equal to or higher than the target temperature specifies a safe mode and thus allows gas flow to be assumed.

If the actual temperature is smaller than the target temperature, no gas flow is assumed and the procedure carries on with step 210. Here, the temperature gradient at the temperature sensor is measured and compared to of the gradient expected with existing gas flow. If the gradient or raise in temperature is larger or equal to a preset threshold gradient or raise of gas flow temperature (GradientGasFlow), gas flow is assumed, see step 240. A preferred threshold gradient may be in the range of about 1° C./10 sec to about 1° C./20 sec. Alternatively, (step 210) it is evaluated whether the actual temperature is larger than or equal to the target temperature plus a temperature difference. Said temperature difference would amount to a tolerance value, e.g. about +2° C., preferably about +1° C. and may be 0° C. If this holds true, gas flow is expected (see step 240).

If the conditions of step 210 are not fulfilled, it is carried on with step 230 which evaluates whether the gradient or fall in temperature is equal to or smaller than the gradient or fall in temperature to be expected if no gas flow occurred. Such assumption is based on a threshold of, e.g., 1° C./10 sec. As with the threshold gradient referred to with regard to step 210, such assumptions and thresholds may vary and depend on the environmental conditions, such as ambient temperature, amount of gas flow, and/or target heating temperatures. Preferably, the threshold(s) is/are based on an assumed normal operation at average ambient temperature and normal gas flow. If this condition is fulfilled, no gas flow is assumed (see step 260). As a consequence, heating may be stopped. After a certain time interval, of preferably about 60 to 180 sec, preferably about 120 sec. and which may vary based on the specific situation, predefined heating impulses or cycles are applied and the temperature response is measured as discussed above. As will be readily understood, such heating cycles are adapted to ensure that, even with no gas flow occurring, no overheating happens.

If the condition of step 230 is not fulfilled, it is carried on with step 250 and it is evaluated whether the sensed temperature gradient is equal to or larger than a negative limit or threshold ('GradientLimitN') and whether the sensed temperature gradient is smaller than or equal to a positive limit or threshold ('GradientLimitP'). In other words, it is evaluated whether the measured temperature gradient lies within predefined boundaries such as, preferably, about +/−0.3° C./10 sec or +/−0.15°/10 sec. If the conditions of step 250 are not fulfilled, a preset interval time, which starts with the first interrogation of step 250, is re-started (step 280) and the procedure of step 250 is repeated after predefined times, e.g. 180 sec. In such situation, gas flow can be expected to occur since the temperature gradient is high, and preferably not 0.

If the conditions of step 250 are fulfilled, and the interval time has not yet expired, the procedure of step 250 is repeated after predefined times as discussed above. If the conditions of step 250 are fulfilled, and the interval time has expired, the system is assumed to run in a steady state. Particularly, here the gradient of the measured temperature is low. This goes along with the risk of missing gas flow and tube overheating. Here, the heating cycle algorithm triggering predefined changes in gas flow temperature and sensing the temperature response curve measured at the temperatures sensor is then run, preferably repeatedly in intervals, which may be predefined or which may depend on the situation (settings, ambient conditions etc.). As already indicated above and as apparent for the skilled person, the applied heating impulses may be negative or positive, i.e., involve a raise or drop in heating power, depending on the situation.

At any time during the above described algorithm, the system may jump back if certain conditions are met which raise doubts as to whether gas flow occurs (see above discussion of insecure gas flow).

Preferably, the algorithm applied and the evaluations made are based on the average control output. Here, the heating pattern triggered in order to achieve a measurable jump in gas temperature preferably involves less than 40% heating during a given time interval and more than 50% heating interruption during said time interval. It will be readily understood by the skilled person, that the specific temperature differences, temperature drops and raises and gradients, heating cycles and heating interruption intervals strongly depend on, i.e. the hose length, hose diameter, gas flow, ambient conditions and/or the individual breathing pattern of the patient. As will also be readily understood, said concept can also be applied to a breathing hose which is heated but not necessarily connected to a humidifier.

This concept easily and advantageously allows ensuring of the existence of a gas flow through the tube thereby preventing the tube's overheating in an easy, reliable and cost-effective manner and emitting alarm signals and/or performing alarm operations in case of danger of overheating.

The algorithm can be applied by means of a separate control unit connected to the hose, as further discussed below as well as by the control unit of an associated device, such as a blower or humidifier. This may involve one hose or two hose systems, while the method can be applied to one or both of these tubes.

To assist in preventing condensation formation a heated respiration tube (such as described in the utility model DE 20 2005 008 156 U2) is coupled with a separate control device which has to control the temperature of the respiratory gas and the tube wall by means of at least one temperature sensor to an adjustable level and thus reduce or prevent the formation of condensate.

A device according to an embodiment of the present technology, which serves for heating gas tubes and which can be coupled to respiration therapy devices and/or respiration devices or also to extracorporeal systems replacing/assisting the lung, consists of at least one control device as well as at least one heated gas tube.

In certain embodiments the control device comprises at least one connection for a temperature measuring device as well as a regulator for controlling the temperature/power of the heating tube, and it is surrounded by a housing which is separate from the housing of the respiration therapy device/ respiration device and also from the humidifier.

In certain embodiments the device is realized such that different heating stages can be selected on the control device.

In certain embodiments each adjustable heating stage is assigned to a defined target temperature when a heating tube with temperature sensor is connected.

In certain embodiments in which a heating tube without temperature sensor is connected, each adjustable heating stage can be assigned to a heating power which should be outputted constantly, wherein this assignment can be stored in the control device or is detected in accordance with an ambient temperature that should optionally be measured, wherein a cooler environment increases the heating power level and vice versa.

In certain embodiments the control device detects an interrupted gas flow or also a newly established gas flow after standstill by means of an analysis of the temperature signal response in case of a temporarily changed power output and then prevents a heat accumulation by an adequate reduction in the mean heating power or automatically activates itself in case of a renewed gas flow.

In certain alternative embodiments an interruption of the gas flow or an establishment of the gas flow is detected by measuring the electrical power input in the respiration therapy device.

In certain embodiments an interruption of the gas flow or an establishment of a gas flow is detected by an additional measurement of the gas volume flow in the tube, preferably by means of a heated sensor element.

In certain embodiments, the state of the device (no gas flow standby/gas flow heating) is preferably signaled optically on the control/operating part.

Figure 5:
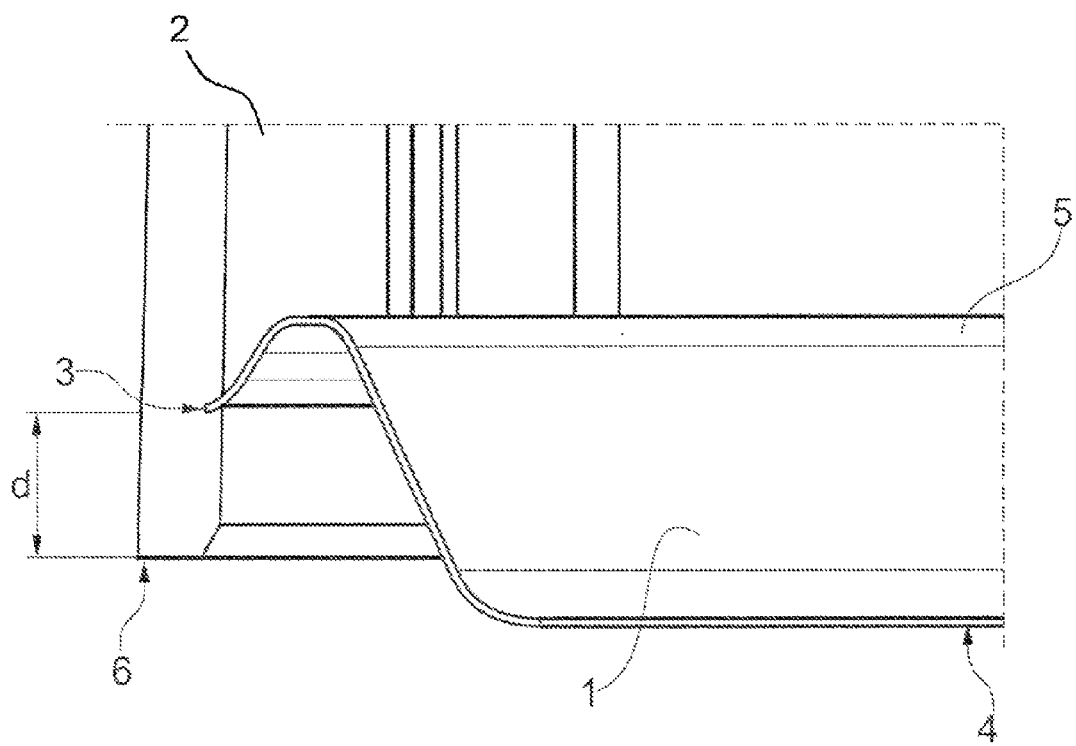
FIG. 5 shows an alternative of the described metal bottom with the sealing concept.

FIG. 5 shows a preferred embodiment of the present technology in a three-dimensional perspective view where a humidifier chamber bottom 1 is suitably mounted to a humidifier chamber component 2. The humidifier chamber bottom 1 is preferably made of a metallic material, such as aluminum or tin plate. The humidifier chamber component, preferably constituting the or at least part of the humidifier chamber side wall, is made of a second material, preferably a thermoplastic resin.

As is apparent from the preferred embodiment as shown in FIG. 5, bottom 1 comprises an outer edge 3 as well as a central portion 4. The outer edge 3 preferably extends along the circumferential periphery. The configuration of the humidifier chamber bottom may be such that the central bottom portion 4 constitutes the lowest part of the humidifier chamber bottom 1 and is adapted for being contacted with a heating plate in use of the humidifier chamber. In its outer circumferential region the humidifier chamber bottom comprises a circumferentially extending crimp or corrugation which is in a raised position vis-à-vis central bottom portion 4 of the humidifier chamber bottom 1 while it is preferred that humidifier chamber bottom outer edge 3 is again lowered vis-à-vis the crest of the crimp 5, as will be further discussed below.

As is apparent from FIG. 5, the lower part of the bottom edge 6 of humidifier chamber component 2 lies, in the mounted state where humidifier chamber bottom 1 is mounted to humidifier chamber component 2, in a raised position vis-à-vis the lower surface, preferably central bottom portion 4, of humidifier chamber bottom 1. In other words, a part of the humidifier chamber bottom 1, here central portion 4, constitutes the lowest part of the humidifier chamber. Said part is preferably planar. Lower end 6 of humidifier chamber component 2 comprises a chamfer or bevel 7, preferably extending along the inner peripheral edge of humidifier chamber component 2 lower end 6. This may ease mounting of bottom 1 to component 2.

Figure 11:
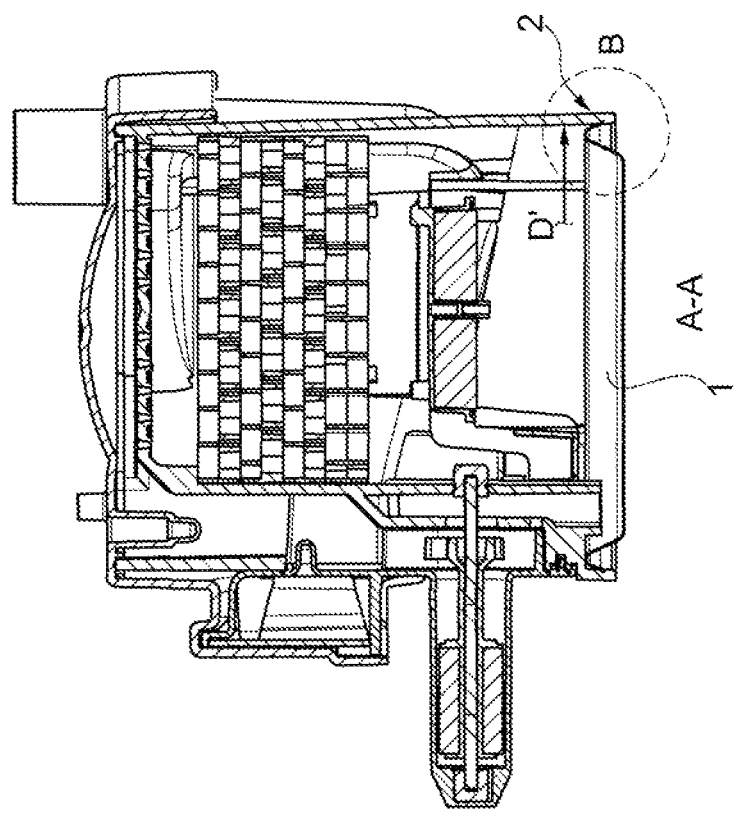
FIG. 11 shows a cross sectional view of the humidifier according to FIG. 10 along line A-A.
Figure 12:
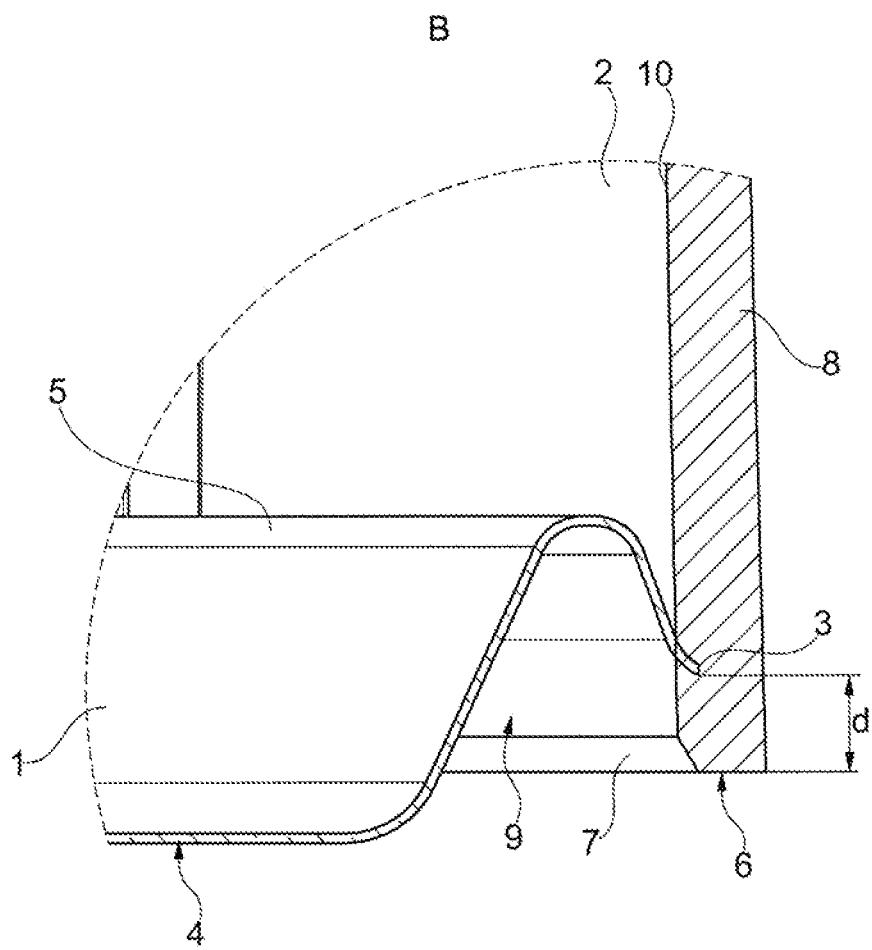
FIG. 12 shows detail B of the humidifier according to FIG. 11.

As can be seen in FIG. 5, the outer edge 3 of humidifier chamber bottom 1 is pressed against and/or into humidifier chamber component 2 at a position preferably being distanced from the lower humidifier chamber component end 6 by at least about 1-10 mm, preferably 1-5 mm, also preferred 1-3 mm. Preferably, the distance between lower end 6 of humidifier chamber component 2 and the position where humidifier chamber bottom edge 3 presses into the material of humidifier chamber component 2 lies in the range between about 1 to 10 mm, preferably about 1 to 4 mm, preferably between about 1.5 and 3 mm. This is also apparent from FIG. 12 showing a corresponding detail of a preferred humidifier chamber according to FIG. 11.

Such construction allows a preferred and beneficial mounting of humidifier chamber bottom 1 into a humidifier chamber component 2, as will be further explained below, leading to an improved, stable, fluid tight and failure safe humidifier chamber.

Humidifier chamber component 2 preferably constitutes a lower part of a humidifier chamber. It may be integral with the humidifier chamber or constitute a part of the humidifier chamber. Humidifier chamber component 2 may comprise a circumferential, preferably round, humidifier chamber wall 8 defining, preferably at its lower edge 6, a humidifier chamber bottom opening 9 for receiving the humidifier chamber bottom 1 which presses against and/or into the inner side 10 of humidifier chamber wall 8.

Humidifier chamber component 2 and humidifier chamber bottom 1 have complementary shapes such that humidifier chamber bottom 1 may be press fit into the humidifier chamber component 2, particularly the humidifier chamber bottom opening 9. Preferably, both humidifier chamber component 2 and humidifier chamber bottom opening 9, particularly inner side 10 of humidifier chamber wall 8 have a generally round, preferably circular cross section. Preferably, inner side 10 of humidifier chamber wall 8 comprises the form of an inner cylinder. Humidifier chamber bottom 1, particularly humidifier chamber bottom edge 3 is generally round, and preferably circular and adapted to fit into humidifier chamber bottom opening 9 and to contact inner side 10 of humidifier chamber wall 8 in a press fit manner. In other words, the diameter D of humidifier chamber bottom 1 is larger than the corresponding diameter D' of humidifier chamber component 2, measured at inner side 10 of humidifier chamber wall 8. Preferably, humidifier chamber bottom diameter D is about 90-120 mm and preferably, about 100-110 mm. However, as will be readily understood by the skilled person, humidifier chamber bottom 1 may have differing diameters. It is preferred, however, that the humidifier bottom diameter D is larger than the corresponding diameter D' of the humidifier chamber bottom opening 9 by preferably about 0.5 to 3 mm.

In a preferred method for manufacturing a humidifier chamber, humidifier chamber bottom 1 is pressed into humidifier chamber bottom opening 9. Thereby, outer edge 3 of humidifier chamber bottom 1 presses against inner side 10 of humidifier chamber wall 8. Once humidifier bottom 1 and humidifier chamber component 2 are in a desired position with regard to one another, pressing is stopped. Next, humidifier chamber bottom 1 is heated such that outer edge 3 of humidifier chamber bottom 1 which is pressed against inner side 10 of humidifier chamber component wall 8 establishes a sealing contact between humidifier chamber bottom 1 and humidifier chamber component 2. Preferably, humidifier chamber bottom 1, particularly humidifier chamber bottom edge 3 melts into the preferably plastic material of humidifier chamber component 2, preferably assisted by the pressure fit between humidifier chamber bottom 1, being elastically deformed, and humidifier chamber component 2 leading to the outer edge 3 of humidifier chamber bottom 1 to urge outwards against and into humidifier chamber bottom component wall 8.

According to a preferred embodiment, humidifier chamber bottom 1 is heated for about 20 seconds to 90 seconds, preferably about 40 seconds to 65 seconds to a temperature lying in the range of about 100 degree Celsius to 200 degree Celsius, preferably 120 degree Celsius to 140 degree Celsius.

Subsequently, upon pressing and heating, positive pressure is applied to the humidifier chamber. Such pressure is preferably applied for approximately 5-60 seconds, particularly preferably for approximately 10-40 seconds. The pressure preferably amounts to approximately 300-500 mbar, particularly preferably to 350-450 mbar and moreover preferably to approximately 400 mbar. Such application of positive pressures subsequently to pressing and heating is optional and may beneficially support and ensure a failure safe fluid tight connection between the humidifier chamber bottom 1 and humidifier chamber component 2.

Humidifier chamber bottom 1 is preferably made of a first material, having a higher melting point than a second material of which humidifier chamber component 2 is made. Preferably, humidifier chamber bottom 1 is made of a material having a higher heat conductivity than the material of the humidifier chamber component. Preferably, the first and second materials of the humidifier chamber bottom and humidifier chamber component are biocompatible. The humidifier chamber bottom 1 is preferably made by deep drawing, hydroforming or similar methods. Humidifier chamber component 2 is preferably injection-molded.

Figure 7:
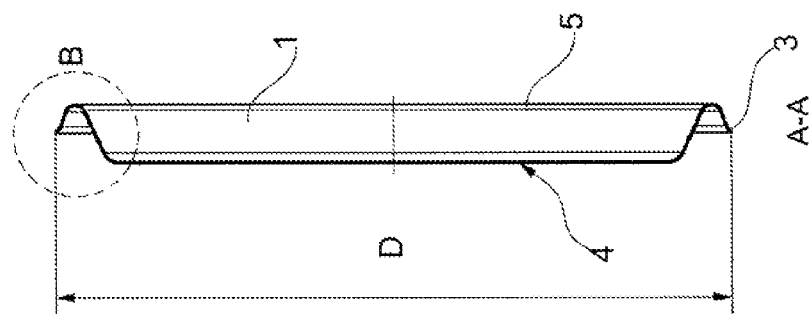
FIG. 7 shows a cross sectional view of the humidifier chamber bottom according to FIG. 6 along line A-A.
Figure 6:
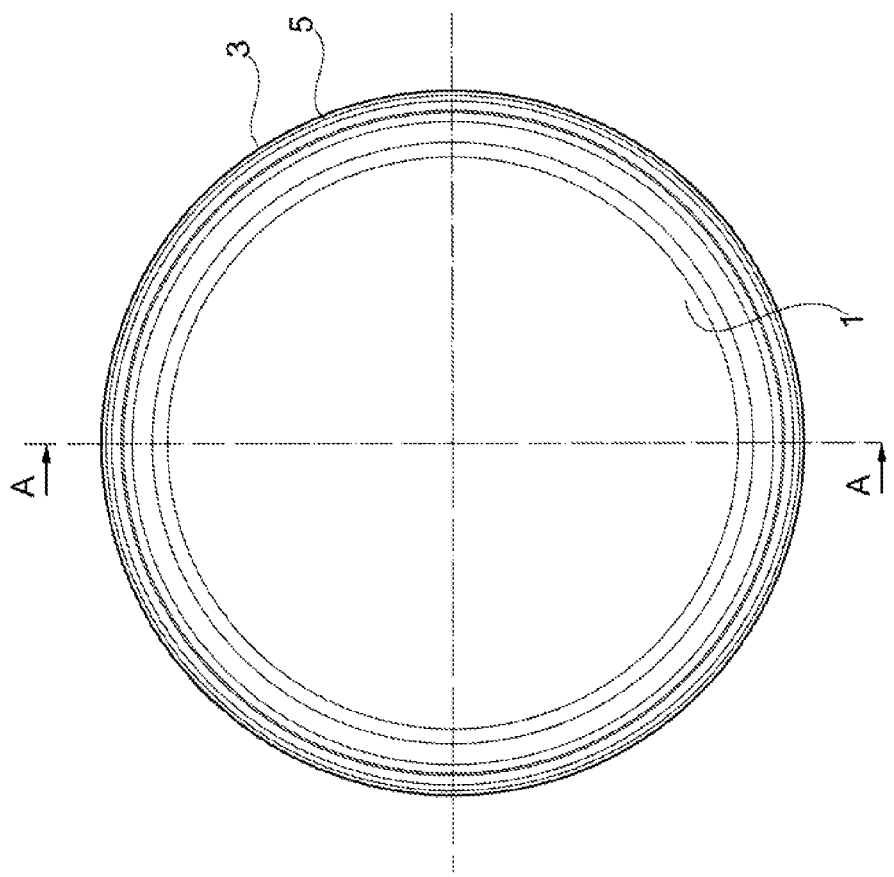
FIG. 6 shows a top view on a humidifier chamber bottom according to the present technology.
Figure 9:
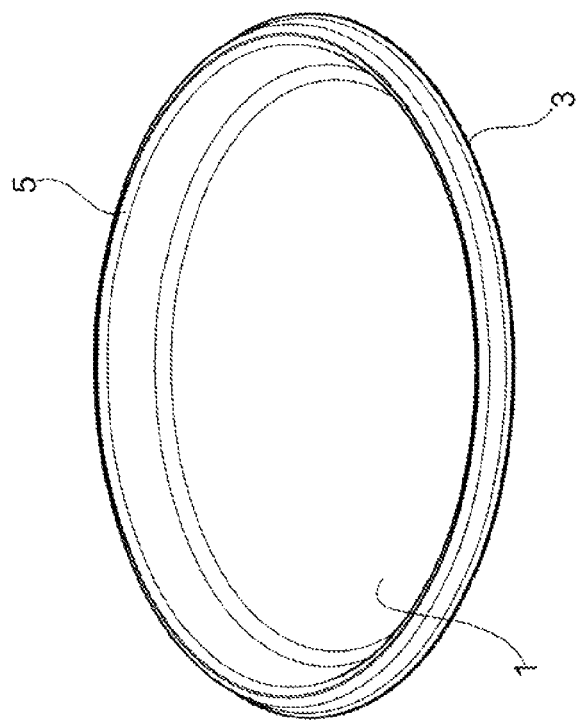
FIG. 9 shows a three-dimensional view of the humidifier chamber bottom according to the present technology.
Figure 8:
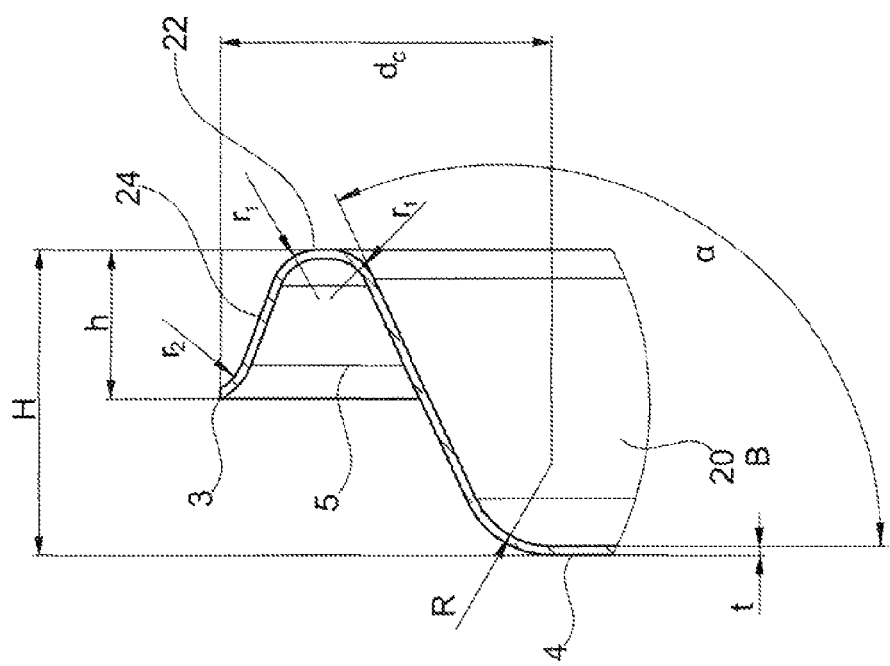
FIG. 8 shows detail B of the humidifier chamber bottom according to FIG. 7.

FIG. 6 shows a top view on humidifier chamber bottom 1 being of circular configuration and having an outer peripheral edge 3 and a circumferentially extending corrugation or crimp adjacent outer edge 3. FIG. 7 shows a cross-sectional view of humidifier chamber bottom 1 along line A-A of FIG. 6 indicating detail B as shown in FIG. 8. Detail B shown in FIG. 8 is generally similar or does generally correspond to the part of humidifier chamber bottom 1 shown in FIG. 5 or 12.

The preferred and beneficial structure of humidifier chamber bottom 1 and particularly crimp or corrugation 5 will now be explained in more detail making general reference to the detail shown in FIG. 8. Humidifier chamber bottom 4 as shown on the left side in FIG. 8 constitutes, in operating position, the lowest part of humidifier chamber bottom 1. Towards the outer circumference of humidifier chamber bottom 1 a corrugation or crimp 5 is provided. This includes a humidifier chamber bottom raising portion 20, circumferentially surrounding central bottom portion 4 and being inclined thereto so that it extends, in an operating position, upwardly from the central bottom portion 4. Preferably, the angle between central bottom portion 4, which is preferably planar, and raising crimp portion 20 lies in the range of about 100-130 degrees, preferably of about 110-120 degrees, such as 112, 113, 114, 115, 116, 117 or 118 degrees. Raising crimp portion 20 extends into a saddle or apex crimp portion 22 which further extends into a lowering or falling crimp portion 24. Apex crimp portion 22 is radiused and preferable has a radius of about 1-3 mm, preferably 1-2 mm. Lowering crimp portion 24 ends at outer circumferential corner 3 of humidifier chamber bottom 1. Preferably, raising crimp portion 20 and lowering or forming crimp portion 24 are, in a cross-sectional view, generally straight and circumferentially extend parallel to outer edge 3. Lowering crimp portion 24 preferably extends to outer edge 3 via a radiused portion. Said radius r2 preferably lies in the range of about 1 mm-2 mm. In other words, the slope of lowering crimp portion 24 is reduced at its lower and outer end where it transmissions into outer edge 3. Outer edge 3 thus extends outwardly away from lowering portion 24.

At is apparent from FIG. 8, the height H of the crimp 5 vis-à-vis central bottom portion 4 and thus the height of humidifier chamber bottom 1 lies in the range of about 7-13 mm, preferably in the range of about 8-11 mm. The width of the crimp 5 as measured from the outer circumference of central bottom portion 4 to the outer edge 3 of humidifier chamber bottom 1 (dc) lies in the range of about 8-12 mm, preferably of about 9-11 mm. The height of the crimp h as measured from the apex 22 to the humidified chamber bottom edge 3 lies in the range of about 3-6 mm, preferably of about 4-5 mm.

Preferably, the thickness of humidifier chamber bottom 1, preferably measured at its central bottom portion 4 is about 0.1-1 mm, preferably about 0.15-0.6 mm and further preferably of about 0.2-0.35 mm (t).

The humidifier chamber bottom's 1 configuration comprising a circumferentially extending crimp or corrugation adjacent outer edge 3, preferably as discussed above with regard to the preferred embodiment shown in FIG. 8, preferably enhances mounting and/or sealing contact of the humidifier chamber bottom 1 and humidifier chamber component 2. In particular, the crimp's configuration is such that a pressure load from the humidifier chamber inside, i.e. from above in operating position, effects a radially outwardly directed movement and/or force of the humidifier chamber bottom outer edge 3. Such movement and/or force is primarily directed against the inner wall 10 of the humidifier chamber component wall 8, thereby increasing the sealing contact between humidifier chamber bottom 1 and humidifier chamber bottom component 2.

Figure 10:
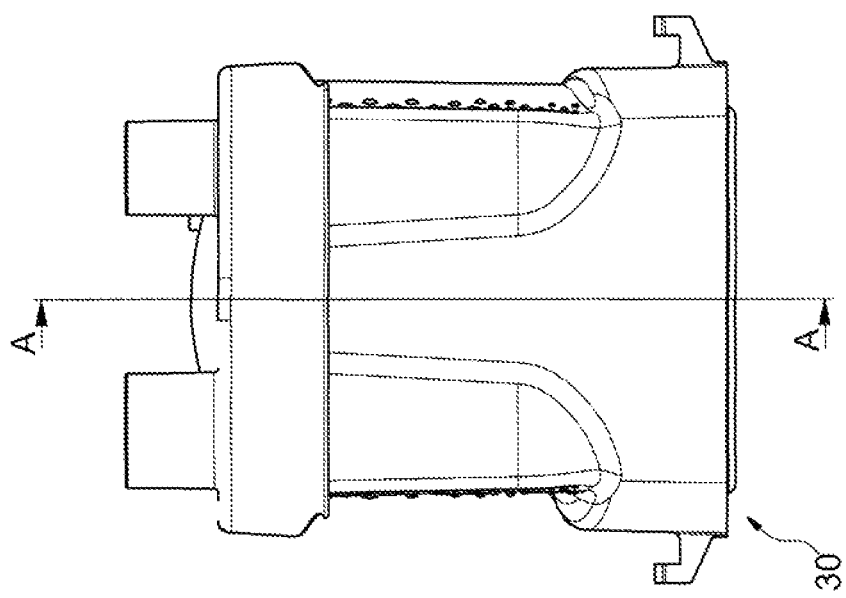
FIG. 10 shows a front view of an exemplary humidifier according to the present technology.

FIG. 10 shows a preferred exemplary humidifier chamber 30. FIG. 11 shows a cross-sectional view of such humidifier chamber 30 along the lines A-A of FIG. 10. FIG. 11 indicates detail B being depicted in and discussed with regard to FIG. 12. A preferred humidifier chamber and humidifier chamber concept together with which the present technology is preferably applied, is disclosed in EP 1 558 877 B1, the disclosure of which relating to the general structure and concept of the discussed humidifier and humidification method is incorporated herewith by reference.

Certain embodiments of the present technology provide an improved method for producing a humidifier chamber as well as an improved humidifier chamber. The humidifier chamber of the present technology is easy and efficient to manufacture in a simple and reliable way due to reduced number of parts and method steps and results in a reliable, robust light and functional humidifier chamber. In particular, it is understood that the pressing and/or melting of the humidifier chamber bottom 1 into the humidifier chamber component 2 effects the fluid and/or liquid-tight seal between humidifier chamber bottom 1 and humidifier chamber component 2. This sealing effect is further improved or at least supported, particularly during use, by the beneficial geometry of humidifier chamber bottom 1 comprising corrugation 5. Particularly, this geometry results in an elastic and predefined pressure directed against humidifier component 2 both during production and use thereby beneficially assisting in establishing and maintaining a sealing contact between humidifier chamber bottom 1 and humidifier chamber component 2.

In the state of the art, further components of the humidifier, such as humidifier lid and humidifier side walls have been connected by means of gluing using adhesives. This has been found cumbersome to manufacture, leading to high manufacturing costs as well as to unsatisfactory results as regards structural stability, hygienic suitability for the desired purpose and optical appearance. There is therefore a need to provide an improved manufacturing method overcoming the above mentioned disadvantages.

According to an embodiment of the technology the humidification chamber further comprises a lid for closing the chamber at the side opposite to the humidifier bottom. Said lid is attached to a humidifier component, preferably to humidifier component 2, which preferably exhibits humidifier side walls circumferentially enclosing the humidifier, i.e., providing the humidifier side walls. Preferably, the geometry of humidifier lid and humidifier component/side walls is such that, in an operating position, the humidifier lid lies on the humidifier side walls, wherein the ends of the side walls abut the lower side of the humidifier lid (in operating position). The lid is preferably made of a material being permeable or non-adsorbent for laser beams used for laser welding in order to allow the lid to be laser-welded to the humidifier side walls. This is necessary in order to allow the laser to penetrate the humidifier lid without being adsorbed by its material which would result in the humidifier lid material being influenced or even destroyed by the laser treatment.

However, in order to allow laser welding of the two, preferably plastic, components, one of them has to adsorb the laser in order to allow welding together of the two components. If the humidifier component is made of a laser adsorbent material, this has been found to lead to satisfactory results as regards structural integrity of the humidifier lid welded to the humidifier side walls while the optical and aesthetical results are unsatisfactory. In particular, it has been found out that the colour of the laser adsorbent humidifier component material changes, which negatively influences the optical and aesthetical appearance of the final product. While this may be negligible for coloured, non-transparent or non-translucent humidifiers, it is of severe negative effect as regards market acceptance for transparent and/or translucent humidifier chambers. According to an embodiment of the present technology it is thus been found out to provide a humidifier lid of a laser permeable or non-adsorbent material and the humidifier component to which the lid is to be welded, such as humidifier side walls which is also made of a laser permeable or non-absorbent material. Particularly, in order to allow welding of the two components which both are non-adsorbent to the laser energy a laser adsorbent sheet is provided between the two parts. Preferably, the laser absorbent sheet closely follows the shape of the contact region between humidifier lid and humidifier component and is located between humidifier lid and humidifier component. Then, laser welding is applied welding together the humidifier lid and the humidifier component including the laser adsorbent sheet interposed between them. This allows an effective, efficient, reliable and cheap manufacturing of a humidification chamber.

The above discussion comprises references to precise or exact terms, features, numerical values or ranges etc. When such terms, features, numerical values or ranges have been mentioned in connection with terms such as, e.g., "about, approximately, around, substantially, essentially, generally, at least" etc. also the exact value is considered encompassed by said statement (i.e., "about 3" is to also include "3" or "substantially radial" is also to include "radial").

The invention claimed is:

1. Humidifier for humidifying medical gases for use in therapy of a patient, comprising a humidification module including a control unit, wherein the humidification module is adapted for receiving a range of different kinds of humidification chambers, and wherein the humidification module is further adapted to sense and/or receive information upon connection of the humidification chamber.

2. Humidifier according to claim 1, wherein the humidification module is further adapted to sense and/or receive information upon connection of additional equipment including hoses and/or a power supply pack.

3. Humidifier according to claim 1, further including one of the range of different kinds of humidification chambers coupled to the humidification module.

4. Humidifier according to claim 1, wherein the different kinds of humidification chambers differ by their humidification concept.

5. Humidifier according to claim 4, wherein the humidification concepts include pass-over humidification, counter-flow humidification, humidification by fluid contact by means of membranes, flash evaporation, bubble humidification and/or wick evaporation, wherein these and/or additional concepts include concepts where liquid and/or gas is moved.

6. Humidifier according to claim 1, wherein the humidification module comprises an interface for mechanically and/or operationally coupling with different kinds of humidification chambers.

7. Humidifier according to claim 1, wherein the humidification module comprises a sensor to sense the kind of humidification chamber connected therewith.

8. Humidifier according to claim 1, wherein the control unit comprises different kinds of operating modes and/or operating algorithms, each operating mode being adapted to specifically operate a humidification chamber.

9. Humidifier according to claim 1, wherein, the humidifier is adapted to operate in an operation mode and/or operating algorithm depending on the kind of and/or on a specific humidification chamber coupled to the humidifier module.

10. Humidifier according to claim 9, wherein the control unit is configured to adapt and/or select an operating mode and/or control algorithm for humidification depending on the humidification chamber sensed by the humidification module.

11. Humidifier according to claim 6, wherein the interface operates by means of mechanical, wired, and/or wireless transmission of information, such information preferably including identification information and/or operation information.

12. Humidifier according to claim 1, wherein the humidification module comprises interfaces for sensing or exchanging information with a connected humidification chamber, the interfaces including one or more of mechanical interface, wired interface including electrical interface, magnetic interface, and wireless interface including optical interface.

13. Humidifier according to claim 1, further comprising a connection for an external power supply unit or an external battery.

14. Humidifier according to claim 1, further adapted to operate additional equipment including one or more respiratory hoses and/or a heating sheath.

15. Humidifier according to claim 1, wherein the humidification chamber comprises identification features allowing identification of the specific kind of humidification chamber and/or a specific humidification chamber by the humidifier.

16. Humidifier according to claim 15, wherein the identification features are provided by one or more interfaces provided on the humidification module.

17. Humidifier according to claim 15, wherein the identification features include demand- or power-associated identification features sensed via a power demand of the humidification chamber.

18. Humidifier according to claim 15, wherein the humidifier is adapted to automatically recognize the humidification chamber connected based on the identification features being unique for each kind of humidification chamber and/or humidification concept; and/or input data;

and to select and/or adapt an operation mode and/or an operation algorithm accordingly.

19. Humidifier according to claim 18, wherein an operating mode and/or control algorithm for humidification includes parameters being dependent on the kind of and/or individual humidification chamber and/or on an individual application, which can be adjusted, the parameters including a maximum lifetime of an individual humidification chamber, a maximum temperature of the heating plate and/or an allocation of priorities.

20. Humidifier according to claim 9, wherein an operating mode and/or control algorithm for humidification includes an allocation of priorities, including prioritizing heating of an inspiration tube vis-à-vis heating of an expiration tube in case a power supply does not allow parallel heating of both the inspiration tube and the expiration tube to a desired extent.

21. Humidifier according to claim 1, wherein the humidification chamber includes an amplitude- and/or frequency-modulated electromagnet for driving a fluid movement device, of different humidification chambers and/or of different humidification concepts.

22. Humidifier according to claim 1, wherein the humidification module comprises a water heater including a heating plate, an induction heater and/or a radiation heater, and/or wherein the humidification module is adapted to connect to and control a heater arranged downstream of a gas flow and close to the patient.

23. Humidifier according to claim 1, wherein the humidification module comprises connections for connecting to sensors provided in and/or on the humidification chamber, and/or wherein the humidification module comprises sensors adapted to be connected to the humidification chamber comprising respective connections.

24. Humidifier according to claim 1, comprising a power supply unit being separate and external from the humidification module.

25. Humidifier according to claim 24, wherein the humidifier is adapted to sense a power supply unit or a battery by means of wired or wireless communication of identification characteristics.

26. Humidifier according to claim 10, wherein the operating mode and/or control algorithm for humidification includes alarm and/or failure prevention functions, depending on an individual humidification chamber connected to the humidification module, including overload and/or excess heating prevention by means of power output adjustment, limitation and/or prioritization.

27. Humidifier according to claim 1, wherein the humidification module comprises a plurality of interfaces for feeding and/or controlling external components, including heated tubes, heated collars and/or sheaths.

28. Humidifier according to claim 25, wherein the humidifier is adapted to individually measure the power consumption or output power for each of a plurality of interfaces, to allow an adapted power output and/or overloading of the power supply or control module.

29. Humidifier according to claim 1, wherein the humidifier comprises interfaces for communication with other medical devices wherein the humidifier is adapted to control and operate the other medical devices, including monitoring systems and/or blowers.

30. Humidification chamber including information on an individual kind of humidification system applied and being adapted to allow humidifier according to claim 1 to sense or receive said information.

31. Humidifier set comprising a humidifier according to claim 1, as well as at least two humidification chambers being of different kinds and/or humidification concepts.

32. Humidifier according to claim 1, further comprising an optical interface for sensing and/or conveying optical information, the optical interface being arranged to be directed to the humidification chamber such that the humidification chamber is illuminated.

33. Humidifier according to claim 32, wherein the optical interface provides optical information on operating parameters, operating conditions, and/or alarms.

34. Humidifier according to claim 32, wherein the optical information is associated with colors, intensity, and/or light or illumination patterns.

35. Humidifier according to claim 34, wherein a first color is used to indicate an error and a second color is used to indicate correct functioning.

36. Humidifier according to claim 35, wherein the first color is red and/or the second color is green.

37. Humidifier according to claim 34, wherein the humidifier is adapted to allow the patient to set the color, intensity and/or illumination pattern for the optical information.

38. Humidifier according to claim 34, wherein the illumination patterns and/or the intensity is preset in the control unit.

39. Method for adapting operation of a humidifier, including sensing of identification features of a humidification chamber by a humidifier comprising a humidification module and a humidification control unit, and choosing and/or adapting, automatically, an operating mode and/or control algorithm for humidification depending on the identification features sensed by the humidifier.

* * * * *